(12) United States Patent
Ju et al.

(10) Patent No.: US 9,890,426 B2
(45) Date of Patent: Feb. 13, 2018

(54) PORE-FORMING PROTEIN CONJUGATE COMPOSITIONS AND METHODS

(71) Applicants: Jingyue Ju, Englewood Cliffs, NJ (US); Zengmin Li, Flushing, NY (US); Sergey Kalachikov, New York City, NY (US); Carl Fuller, Berkeley Heights, NJ (US)

(72) Inventors: Jingyue Ju, Englewood Cliffs, NJ (US); Zengmin Li, Flushing, NY (US); Sergey Kalachikov, New York City, NY (US); Carl Fuller, Berkeley Heights, NJ (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 15/439,173

(22) Filed: Feb. 22, 2017

(65) Prior Publication Data

US 2017/0175183 A1    Jun. 22, 2017

Related U.S. Application Data

(63) Continuation of application No. 15/064,555, filed on Mar. 8, 2016, now abandoned.

(60) Provisional application No. 62/130,326, filed on Mar. 9, 2015.

(51) Int. Cl.
| | | |
|---|---|---|
| C12Q 1/68 | (2006.01) |
| C07K 14/31 | (2006.01) |
| C12N 9/12 | (2006.01) |
| C12N 9/96 | (2006.01) |

(52) U.S. Cl.
CPC .......... *C12Q 1/6874* (2013.01); *C07K 14/31* (2013.01); *C12N 9/1252* (2013.01); *C12N 9/96* (2013.01); *C12Y 207/07007* (2013.01)

(58) Field of Classification Search
None
See application file for complete search history.

(56) References Cited

U.S. PATENT DOCUMENTS

| | | | |
|---|---|---|---|
| 6,664,079 B2 | 12/2003 | Ju et al. |
| 7,345,159 B2 | 3/2008 | Ju et al. |
| 7,635,578 B2 | 12/2009 | Ju et al. |
| 7,713,698 B2 | 5/2010 | Ju et al. |
| 7,790,869 B2 | 9/2010 | Ju et al. |
| 7,883,869 B2 | 2/2011 | Ju et al. |
| 7,982,029 B2 | 7/2011 | Ju et al. |
| 8,088,575 B2 | 1/2012 | Ju et al. |
| 8,298,792 B2 | 10/2012 | Ju et al. |
| 8,796,432 B2 | 8/2014 | Ju et al. |
| 8,889,348 B2 | 11/2014 | Ju |
| 9,115,163 B2 | 8/2015 | Ju et al. |
| 9,133,511 B2 | 9/2015 | Ju et al. |
| 9,169,510 B2 | 10/2015 | Ju et al. |
| 9,175,342 B2 | 11/2015 | Ju et al. |
| 9,255,292 B2 | 2/2016 | Ju et al. |
| 9,297,042 B2 | 3/2016 | Ju et al. |
| 9,528,151 B2 | 12/2016 | Ju et al. |
| 9,605,309 B2 | 3/2017 | Davis et al. |
| 9,624,539 B2 | 4/2017 | Ju et al. |
| 9,670,539 B2 | 6/2017 | Ju et al. |
| 2010/0304381 A1 | 12/2010 | Taing et al. |
| 2015/0111759 A1 | 4/2015 | Ju et al. |
| 2015/0119259 A1 | 4/2015 | Ju et al. |
| 2015/0368710 A1 | 12/2015 | Fuller et al. |
| 2016/0024570 A1 | 1/2016 | Ju et al. |
| 2016/0041179 A1 | 2/2016 | Ju et al. |
| 2016/0264612 A1 | 9/2016 | Ju et al. |
| 2017/0058335 A1 | 3/2017 | Tao et al. |
| 2017/0101675 A1 | 4/2017 | Ju et al. |

FOREIGN PATENT DOCUMENTS

| | | |
|---|---|---|
| WO | 2002/022883 | 3/2002 |
| WO | 2002/029003 | 4/2002 |
| WO | 2007/002204 | 1/2007 |
| WO | 2007/053702 | 5/2007 |
| WO | 2007/053719 | 5/2007 |
| WO | 2007/146158 | 12/2007 |
| WO | 2008/069973 | 6/2008 |
| WO | 2009/051807 | 4/2009 |
| WO | 2009/054922 | 4/2009 |
| WO | 2012/162429 | 11/2012 |
| WO | 2013/154999 | 10/2013 |
| WO | 2013/191793 | 12/2013 |
| WO | 2014/081301 | 4/2014 |
| WO | 2014/081303 | 5/2014 |
| WO | 2014/117001 | 7/2014 |
| WO | 2014/144883 | 9/2014 |
| WO | 2014/144898 | 9/2014 |

(Continued)

OTHER PUBLICATIONS

U.S. Appl. No. 15/064,444, Ju et al.
U.S. Appl. No. 15/449,757, Kalachikov et al.
Restriction Requirement dated Jan. 5, 2017 in connection with U.S. Appl. No. 14/391,320, Ju et al.
Response to Restriction Requirement dated May 4, 2017 in connection with U.S. Appl. No. 14/391,320, Ju et al.
Non-Final Office Action dated May 31, 2017 in connection with U.S. Appl. No. 14/391,320, Ju et al.

(Continued)

*Primary Examiner* — Christopher M Gross
(74) *Attorney, Agent, or Firm* — John P. White; Cooper & Dunham LLP

(57) ABSTRACT

The present disclosure relates to compositions and methods based on a fast, efficient chemical reaction for conjugating a pore-forming protein, such as α-hemolysin, to a biomolecule, such as antibodies, receptors, and enzymes, such as DNA polymerase, and the use of such pore-forming protein conjugates in nanopore devices and methods.

18 Claims, 3 Drawing Sheets

(56) References Cited

FOREIGN PATENT DOCUMENTS

| WO | 2015/123430 | 8/2015 |
|---|---|---|
| WO | 2015/148402 | 10/2015 |
| WO | 2015/179284 | 11/2015 |
| WO | 2016/144973 | 9/2016 |
| WO | 2016/154215 | 9/2016 |

OTHER PUBLICATIONS

International Search Report and Written Opinion of the International Searching Authority dated Oct. 25, 2013 in connection with PCT International Application No. PCT/US2013/035635.
Communication pursuant to Rule 164(1) EPC dated Dec. 7, 2015 by the EPO in connection with EP 13775787.8.
Extended European Search Report dated Mar. 11, 2016 by the EPO in connection with EP 13775787.8.
Oct. 10, 2016 Amendment in Response to the Extended European Search Report dated Mar. 11, 2016 by the EPO in connection with EP 13775787.8.
Feb. 9, 2017 Communication Pursuant to Article 94(3) EPC, issued by the European Patent Office in connection with EP 13775787.8.
Mar. 16, 2016 Restriction Requirement issued in connection with U.S. Appl. No. 14/391,337.
Sep. 16, 2016 Response to the Mar. 16, 2016 Restriction Requirement issued in connection with U.S. Appl. No. 14/391,337.
Office Action dated Oct. 26, 2016 in connection with U.S. Appl. No. 14/391,337, Ju et al.
Apr. 25, 2017 Amendment in Response to the Oct. 26, 2016 Office Action issued in connection with U.S. Appl. No. 14/391,337, Ju et al.
Final Office Action dated May 25, 2017 in connection with U.S. Appl. No. 14/391,337, Ju et al.
International Search Report and Written Opinion of the International Searching Authority dated Sep. 24, 2013 in connection with PCT International Application No. PCT/US2013/035630.
Communication pursuant to Rule 164(1) EPC dated Dec. 2, 2015 by the EPO in connection with EP 13807639.3.
Extended European Search Report dated Mar. 11, 2016 by the EPO in connection with EP 13807639.3.
Oct. 10, 2016 Amendment in Response to the Extended European Search Report dated Mar. 11, 2016 by the EPO in connection with EP 13807639.3.
Communication Pursuant to Article 94(3), dated Feb. 9, 2017 by the European Patent Office in connection with EP 13807639.3.
Aug. 4, 2015 Applicant Statement in connection with U.S. Appl. No. 14/666,124 regarding Amendments to p. 40 Regarding Tagged Nucleotides.
International Search Report and Written Opinion of the International Searching Authority dated Jun. 29, 2015 in connection with PCT International Application No. PCT/US2015/022063.
International Preliminary Report on Patentability (Chapter II of the Patent Cooperation Treaty), dated Mar. 6, 2016 in connection with PCT International Application No. PCT/US2015/022063.
International Search Report dated May 20, 2016 in connection with WO2016/144973, The Trustees of Columbia University in the City of New York, Ju et al.
Written Opinion of the International Searching Authority dated May 20, 2016 in connection with WO2016/144973, The Trustees of Columbia University in the City of New York, Ju et al.
International Search Report dated Aug. 8, 2016 in connection with WO2016/154215, The Trustees of Columbia University in the City of New York, Ju et al.
Fuller et al., "Real-time single-molecule electronic DNA sequencing by synthesis using polymer-tagged nucleotides on a nanopore array", PNAS, vol. 113, No. 19, pp. 5233-5238, published May 10, 2016; doi/10.1073.
Lang, K. & Chin, J. "Bioorthogonal Reactions for Labeling Proteins", ACS Chem. Biol. 2014, vol. 9, pp. 16-20.
Stranges et al., "Design and characterization of a nanopore-coupled polymerase for single-molecule DNA sequencing by synthesis on an electrode array", Proc Natl Acad Sci USA, Oct. 11, 2016. doi:10/1073/PNAS.1608271113.

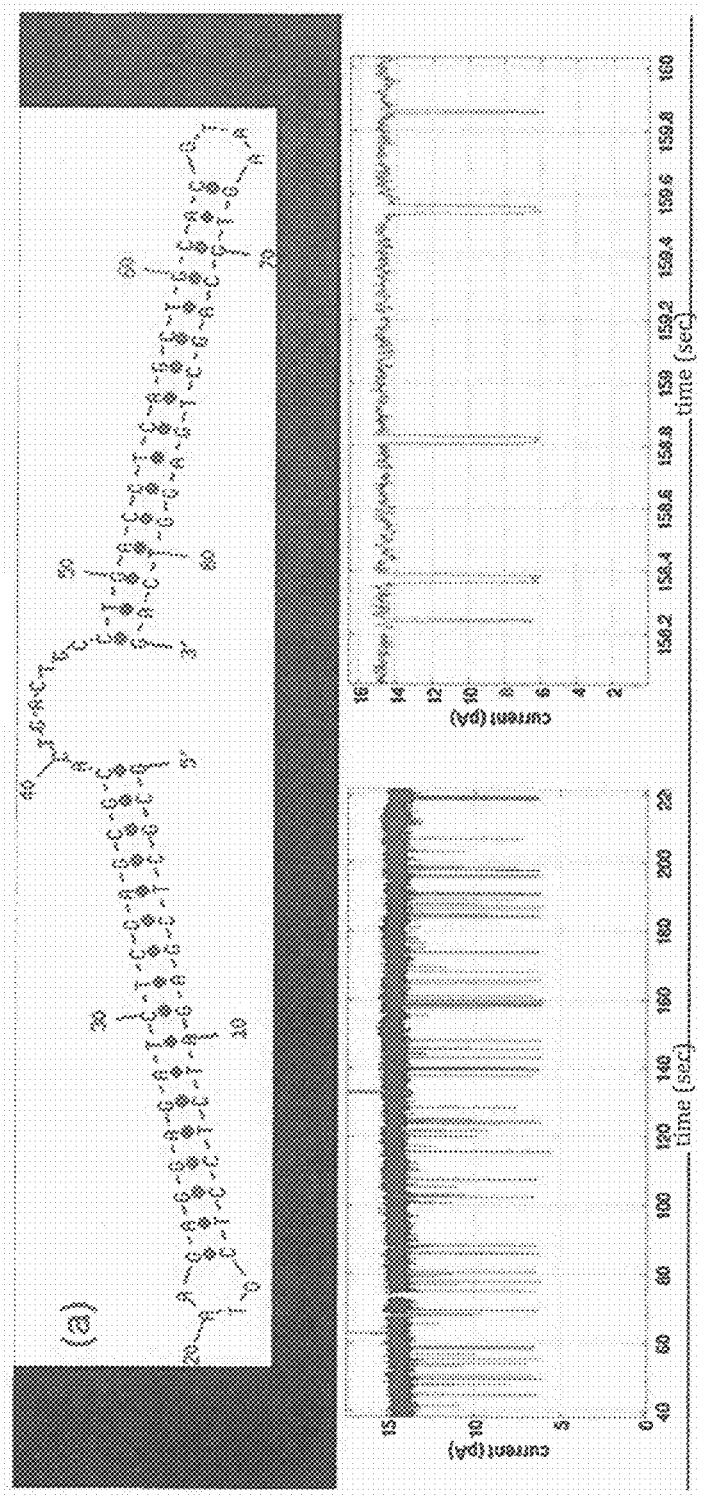

PORE-FORMING PROTEIN CONJUGATE COMPOSITIONS AND METHODS

This application is a continuation of U.S Ser. No. 15/064,555, filed Mar. 8, 2016, now allowed, which claims priority of U.S. Provisional Application No. 62/130,326, filed Mar. 9, 2015, the entire content of each of which are incorporated herein by reference.

This invention was made with government support under grant HG007415 awarded by NIH. The government has certain rights in the invention.

TECHNICAL FIELD

The present disclosure relates to fast, efficient chemical reactions for conjugating pore-forming proteins, such as α-hemolysin, to biomolecules, such as antibodies, receptors, and enzymes, such as DNA polymerase.

INCORPORATION BY REFERENCE

Throughout this application, various publications and patents are referenced. Full citations for these references may be found at the end of the specification immediately preceding the claims. The disclosures of these publications and patents in their entirety are hereby incorporated by reference into this application to more fully describe the state of the art to which this invention pertains.

BACKGROUND

"Click" chemistry refers to a class of chemical reactions that are capable of quickly and efficiently forming covalent linkages between molecules. A variety of click chemical reactions are known, and many have been employed to conjugate biomolecules. In many cases, the click chemistry used to conjugate biomolecules is also "bio-orthogonal," which means that reaction can occur in a biological system without interfering substantially with the normal biochemical function of that system. Such bio-orthogonal click reactions have been used extensively for in vivo labeling of biomolecules.

Single-molecule sequencing-by-synthesis (SBS) techniques using nanopores have been developed. See e.g., US Pat. Publ. Nos. 2013/0244340 A1 and 2013/0264207 A1. Nanopore SBS involves the use of a polymerase synthesize a DNA strand complementary to a target sequence template and determine the identity of each nucleotide monomer as it is added to the growing strand, thereby determining the target sequence. Each added nucleotide monomer is detected via a nanopore located adjacent to the polymerase active site and the growing strand. Obtaining an accurate signal requires proper positioning of a polymerase active site near a nanopore. Proper positioning typically is achieved by covalently linking the polymerase to the pore-protein that makes up the nanopore.

Monomeric pore-forming proteins have molecular weights range from as little as 5 kDa to 80 kDa, and these monomers form large multimeric complexes of 6, 7, 8, 9, 10, or more monomers, having molecular weights of 160, kDa, 180 kDa, 200 kDa, 220 kDa, or more. Under suitable conditions these multimeric complexes spontaneously form pores through lipid bilayer membranes. The well-studied pore-forming protein, α-hemolysin (from *S. aureus*) has a monomer molecular weight of 33 kDa and spontaneously forms a heptameric pore complex having a molecular weight of 231 kDa. Polymerases are large proteins that range in molecular weight from about 60 kDa to 100 kDa and even much larger multimeric complexes in some cases (e.g., RNA polymerase ~400 kDa multimer). The Klenow fragment of DNA polymerase I has a molecular weight of 68 kDa.

Accordingly, the kinetics of any reaction to conjugate these pore-forming proteins, like the α-hemolysin heptamer, to large biomolecules, like DNA polymerase, in order to provide a nanopore sensor will be extremely limited by the low concentration achievable (and relative low amounts available with such large macromolecules. The maximum solubility of such large proteins in aqueous solution typically is limited to approximately 0.1 to 10 mg/mL. Thus, the concentration of the two macromolecules in solution used for a conjugation reaction is limited to ~1 µM to 1000 µM. For example, the α-hemolysin protein pore consists of 7 identical subunits totaling about 235,000 molecular weight. Thus a solution of 10 mg/ml has a concentration of about 42 µM. This relatively low concentration range effectively limits viable conjugation chemistries to those having extremely fast, irreversible reaction rates.

The typical Cu-catalyzed "click" (azide-alkyne Huisgen cylcoaddition) chemistry is both slow and requires a copper (Cu) catalyst that can inactivate proteins and enzymes (See e.g., Wang et al. (2003) and Presolski et al. (2011)). More recently, copper-free cycloaddition involving alkynes and asides have been developed (See e.g., Jewett and Bertozzi (2010)). These Cu-free reactions, however, are too slow for practical conjugation reactions between two large protein molecules, and can require 3-4 days to provide a significant yield of conjugates. Many proteins of interest, particularly enzymes such as polymerases, cannot withstand such long reaction times.

Due to the relatively low-concentrations of pore-protein and polymerase typically used in forming a nanopore detector for SBS, it is important that a highly efficient and selective chemical "click" reaction is developed allowing strong, selective, covalent conjugation between the two. Thus, there remains a need for faster and more efficient chemical processes to manufacture the polymerase-pore structures used in nanopore sequencing.

SUMMARY

The present disclosure provides compositions of a conjugate between a pore-forming protein and a biomolecule, and chemical processes for preparing such pore-forming protein conjugates, and their incorporation in nanopores and associated uses, including use in nanopore sequencing.

In some embodiments, the present disclosure provides a composition comprising a compound of formula (I)

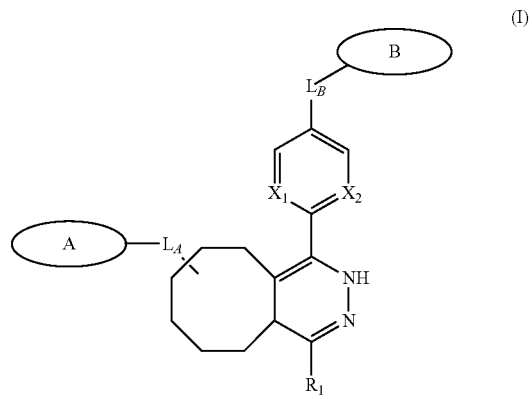

wherein, one of A and B is a pore-forming protein, and the other a biomolecule selected from the group consisting of an enzyme, an oligonucleotide (e.g., of at least about 20 nucleotides), an antibody, and a receptor; $L_A$ and $L_B$ are linkers; $X_1$ and $X_2$ are atoms independently selected from C and N; and $R_1$ is a chemical group selected from the group consisting of: H, F, Cl, Br, I, $CH_3$, $CF_3$, $NH_2$, $NO_2$, OH, C(O)OH, $C(O)OCH_3$, $C(O)NH_2$, linear or branched ($C_2$-$C_5$) alkyl, linear or branched ($C_2$-$C_5$) alkenyl, linear or branched ($C_2$-$C_5$) alkynyl, unsubstituted or para-substituted 6-membered aryl ring, and unsubstituted or para-substituted 6-membered heteroaryl ring. In some embodiments, the composition further comprises an aqueous solution.

In some embodiments, the present disclosure provides a nanopore composition comprising a compound of formula (I), wherein one of A and B is a pore-forming protein is part of a nanopore. In same embodiments, the nanopore is embedded in a membrane, and optionally, the membrane can be attached to a solid substrate, and/or is formed such that it spans a well or depression or hole in a solid substrate, which optionally comprises a material selected from the group consisting of polymer, glass, silicon, and a combination thereof. In some embodiments, the solid substrate further comprises adjacent to the nanopore a sensor, a sensing circuit, or an electrode coupled to a sensing circuit, optionally, a complementary metal-oxide semiconductor (CMOS), or field effect transistor (FET) circuit.

In some embodiments, the present disclosure provides a method of preparing a composition comprising a compound of formula (I), wherein the method comprises contacting under suitable reaction conditions: (a) a tetrazine-linker-conjugate compound of formula (II)

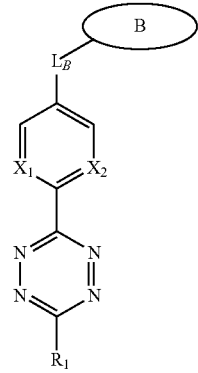

(II)

and (b) a trans-cyclooctene (TCO)-linker-conjugate compound of formula (III),

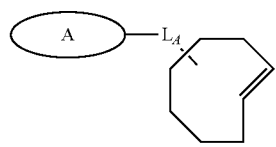

(III)

wherein, one of A and B is a pore-forming protein, and the other is a biomolecule capable of catalyzing the synthesis of a nucleotide polymer; $L_A$ and $L_B$ are linkers; $X_1$ and $X_2$ are atoms independently selected from C and N; and $R_1$ is a chemical group selected from the group consisting of: H, F, Cl, Br, I, $CH_3$, $CF_3$, $NH_2$, $NO_2$, OH, C(O)OH, $C(O)OCH_3$, $C(O)NH_2$, linear or branched ($C_2$-$C_5$) alkyl, linear or branched ($C_2$-$C_5$) alkenyl, linear or branched ($C_2$-$C_5$) alkynyl, unsubstituted or para-substituted 6-membered aryl ring, and unsubstituted or para-substituted 6-membered heteroaryl ring; and whereby the contacted compounds of formula (II) and formula (III) undergo an inverse electron demand Diels-Alder (IEDDA) reaction to form a conjugate of the pore-forming protein and the biomolecule.

In some embodiments, the present disclosure provides a method of preparing a conjugate of a pore-forming protein and a biomolecule capable of catalyzing the synthesis of a nucleotide polymer, said method comprising the steps of: (a) contacting a pore-forming protein with a tetrazine-linker-maleimide compound of formula (V) under suitable reaction conditions:

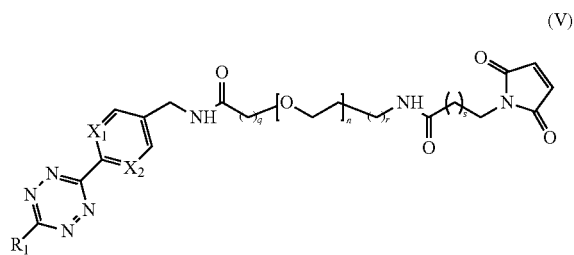

(V)

wherein, $X_1$ and $X_2$ are atoms independently selected from C and N; $R_1$ is a chemical group selected from the group consisting of: H, F, Cl, Br, I, $CH_3$, $CF_3$, $NH_2$, $NO_2$, OH, C(O)OH, $C(O)OCH_3$, $C(O)NH_2$, linear or branched ($C_2$-$C_5$) alkyl, linear or branched ($C_2$-$C_5$) alkenyl, linear or branched ($C_2$-$C_5$) alkynyl, unsubstituted or para-substituted 6-membered aryl ring, and unsubstituted or para-substituted 6-membered heteroaryl ring; and n=1 to 50, and q, r, and s each independently=0, 1, 2 or 3; thereby forming a tetrazine-linker-pore-forming protein conjugate;

(b) contacting a biomolecule capable of catalyzing the synthesis of a nucleotide polymer with a trans-cyclooctene-linker-maleimide compound of formula (VI) under suitable reaction conditions,

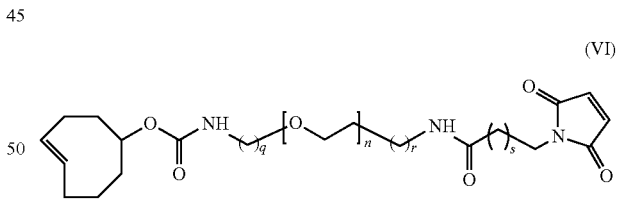

(VI)

wherein, n=1 to 50, and q, r, and s each independently=0, 1, 2 or 3; thereby forming a TCO-linker-biomolecule conjugate; and (c) contacting the tetrazine-linker-pore-forming protein conjugate of step (a) with the TCO-linker-biomolecule conjugate of step (b) under suitable reaction conditions, whereby the two conjugates undergo an inverse electron demand Diels-Alder reaction to form a conjugate of the pore-forming protein and the biomolecule.

In embodiments of the compositions and methods of preparation disclosed herein, the pore-forming protein is selected from the group consisting of α-hemolysin, β-hemolysin, γ-hemolysin, aerolysin, cytolysin, leukocidin, melittin, MspA porin, and porin A. In one embodiment, the pore-forming protein is α-hemolysin from *Staphylococcus aureus*. In one embodiment, the pore-forming protein is α-hemolysin C46 ("α-HL C46"), which comprises α-hemolysin from *S. aureus* with a K46C amino acid residue substitution. In some embodiments, the pore-forming protein is capable of forming a nanopore of diameter of about 0.5 nanometer to about 25 nanometers.

In some embodiments of the methods of preparation of the conjugate compositions of formula (I), the pore-forming protein and/or the biomolecule are present in the reaction solution at a concentration of less than 1000 µM, 750 µM, 500 µM, 250 µM, 100 µM, 50 µM, 10 µM, 5 µM, or 1 µM or less.

In some embodiments of the compositions and methods of preparation disclosed herein, the pore-forming protein has a molecular weight of at least 20 kDa, 30 kDa, 40 kDa, 50 kDa, or greater. In some embodiment of the composition, the biomolecule has a molecular weight of at least 30 kDa, 40 kDa, 50 kDa, 60 kDa, 70 kDa, 80 kDa, or greater. In some embodiments, the pore-forming protein has a molecular weight of at least 30 kDa and the biomolecule has a molecular weight of at least 50 kDa.

In some embodiments of the compositions and methods of preparation disclosed herein, the pore-forming protein is a part of a multimeric complex, wherein the multiuser is selected from hexamer, heptamer, octamer, nonamer, decamer, or larger multimer. In some embodiments, the pore-forming protein is a single monomer which is part of a multimeric complex, wherein the other monomers of the complex do not comprise a composition of formula (I) (i.e., only a single monomer of the multimer is conjugated to the biomolecule).

In some embodiments of the compositions and methods of preparation disclosed herein, the pore-forming protein is embedded in a membrane. In some embodiments, the pore-forming protein is part of a nanopore. In some embodiments, the pore-forming protein is attached to a solid substrate, and optionally the solid substrate comprises a material selected from the group consisting of polymer, glass, silicon, and a combination thereof.

In some embodiments of the compositions and methods of preparation disclosed herein, the biomolecule is an enzyme capable of catalyzing the synthesis of at polymer. In some embodiments, the biomolecule is an enzyme selected from the group consisting of a DNA polymerase, RNA polymerase, reverse transcriptase, and DNA ligase. In some embodiments, the biomolecule is a naturally-occurring or non-naturally occurring (e.g., engineered) enzyme that has 5'→3' DNA polymerase activity and strong strand displacement activity but lacks 5'→3' exonuclease activity. In some embodiments, the biomolecule comprises a DNA polymerase from *Bacillus stearothermophilus*. In some embodiments, the biomolecule comprises the large fragment of DHA polymerase from *B. stearothermophilus*. In one embodiment, the biomolecule is Bst 2.0 DNA polymerase. In some embodiments, the biomolecule is 9° N polymerase, *E. Coli* DNA Polymerase I, Bacteriophage T4 DNA polymerase, Sequenase, Taq DNA polymerase, 9° N polymerase (exo-)A485L/Y409V or Phi29 DNA polymerase (φ29 DNA Polymerase).

In some embodiments of the compositions and methods of preparation comprising a compound of formula (I), the $X_1$ and $X_2$ atoms are each C, and $R_1$ is a $CH_3$ group. In some embodiments, one or both of the $X_1$ and $X_2$ atoms are N. In some embodiments, $R_1$ is an unsubstituted or para-substituted 6-membered aryl ring, or an unsubstituted or para-substituted 6-membered heteroaryl ring selected from the group consisting of: phenyl, benzoic acid, 4-methyl-phenyl, 4-methoxy-phenyl, 4-trifluoromethyl-phenyl, 2-pyridyl, 2-pyridyl-4-methyl, 2-pyridyl-4-carboxylic acid, 2-pyrimidyl, 2-pyrimidyl-4-methyl, and 2-pyrimidyl-4-carboxylic acid.

In some embodiments of the compositions and methods of preparation comprising a compound of formula (I), the compound of formula (I) is a compound of any one of formula (Ia) through formula (Iq), as disclosed herein.

In some embodiments of the compositions and methods of preparation comprising a compound of formula (I), the linkers $L_A$ and $L_B$ comprise a covalently bonded chain of 2 to 100 atoms comprising one or more of the following chemical groups: linear ($C_1$-$C_5$) alkyl, linear ($C_1$-$C_5$) alkenyl, linear ($C_1$-$c_5$) alkynyl, ester, ether, amine, amide, imide, phosphodiester, and/or polyethylene glycol (PEG). In some embodiments, the linkers $L_A$ and $L_B$ attach to A and B either through a thioether bond to a sulfhydryl group on A and/or B, or through a peptide bond to a primary amine group of A and/or B. In some embodiments, the linkers $L_A$ and $L_B$ comprise a polymer of from 1 to 50 polyethylene glycol (PEG) moieties.

In some embodiments of the compositions and methods of preparation comprising a compound of formula (I), the linkers $L_A$ and $L_B$ are independently selected from the group consisting of structures of formula (IVa)-formula (IVd).

BRIEF DESCRIPTION OF THE FIGURES

FIG. 3 depicts nucleotide binding experiments with nanopore detection using a primer/template DNA (a) and the conjugate between pore-forming protein α-HL-C46, and the DNA polymerase, Bst 2.0, via the IEDDA reaction using TCO-linker-maleimide and 6-Me-TZ-linker-maleimide reagents, as described in Example 1.

DETAILED DESCRIPTION

Figure 1:
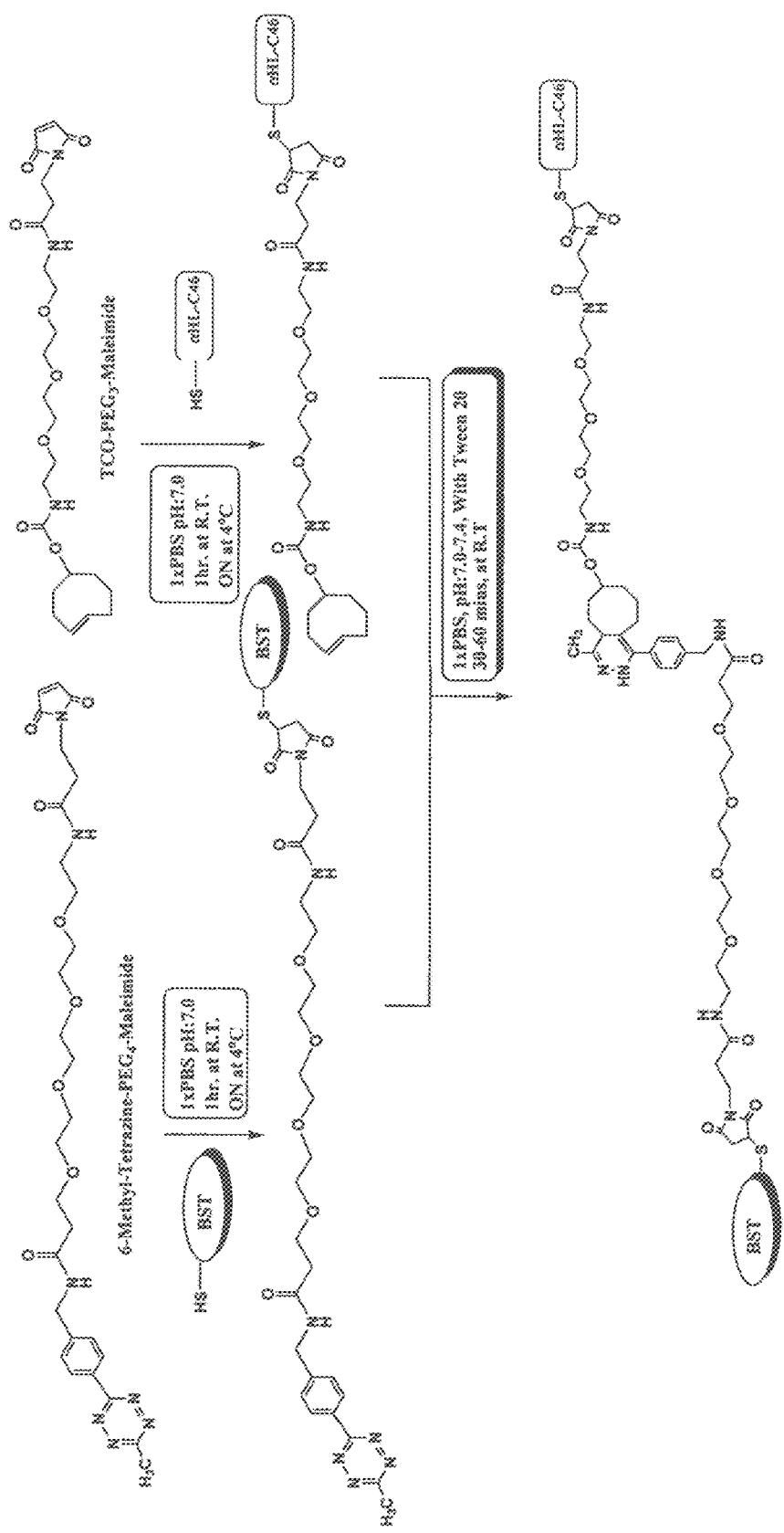
FIG. 1 depicts a schematic illustration of the reactions used in forming the conjugate between the pore-forming protein, α-HL-C46, and the DNA polymerase, Bst 2.0, via the IEDAA reaction using TCO-linker-maleimide and 6-Me-TZ-linker-maleimide reagents, as described in Example 1.

The present disclosure is directed to compositions comprising conjugates between pore-forming proteins (e.g., α-hemolysin) and other biomolecules, including enzymes (e.g., DNA polymerase), oligonucleotides (e.g., single-stranded 20-mer oligonucleotides), antibodies and receptors. The conjugates are prepared using an inverse electron demand Diels-Alder (IEDDA) "click" reaction between a pair of conjugation reagents: one comprising trans-cyclooctene moiety and the other comprising a tetrazine moiety. The disclosed IEDDA reagents allow for fast, efficient conjugation between pore-forming proteins and other biomolecules at relatively low concentrations and without large molar excesses of one reagent over the other. Accordingly, the compositions and chemical processes for preparing the conjugates disclosed herein are particularly well-suited for use in preparing nanopore compositions comprising a pore-forming protein embedded in a membrane covalently linked to a biomolecule, such as a DNA polymerase. Such nanopore compositions can be used in applications requiring nanopore detection, including single-molecule DNA sequencing-by-synthesis.

For the descriptions herein and the appended claims, the singular forms "a", and "an" include plural referents unless the context clearly indicates otherwise. Thus, for example, reference to "a protein" includes more than one protein, and reference to "a compound" refers to more than one compound. The use of of "comprise," "comprises," "comprising" "include," "includes," and "including" are interchangeable and not intended to be limiting. It is to be further understood that where descriptions of various embodiments use the term "comprising," those skilled in the art would understand, that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example "1 to 50" includes "2 to 25", "5 to 20", "25 to 50," "1 to 10", etc.

It is to be understood that both the foregoing general description, including the drawings, and the following detailed description are exemplary and explanatory only and are not restrictive of this disclosure.

Definitions

The technical and scientific terms used in the descriptions herein will have the meanings commonly understood by one of ordinary skill in the art, unless specifically defined otherwise. Accordingly, the following terms are intended to have the following meanings.

"Protein", "polypeptide," and "peptide" are used interchangeably herein to denote a polymer of at least two amino acids covalently linked by an amide bond, regardless of length or post-translational modification (e.g., glycosylation, phosphorylation, lipidation, myristilation, ubiquitination, etc.).

"Pore-forming protein," "pore-forming toxin," or "pore protein," as used herein refers to a natural or non-naturally occurring protein capable of forming a pore or channel structure in a barrier material such as a lipid bilayer or cell membrane. The terms as used herein are intended to include both a pore-forming protein in solution, and a pore-forming protein embedded in a membrane or barrier material, or immobilized on a solid substrate or support. The terms as used herein are intended to including pore-forming proteins as monomers and also as any multimeric forms into which they are capable of assembling. Exemplary pore-forming proteins that may he used in the compositions and methods of the present disclosure include α-hemolysin (e.g., from S. aureus), β-hemolysin, γ-hemolysin, aerolysin, cytolysin (e.g., pneumolysin), leukocidin, melittin, and porin A (e.g., MspA from Mycobacterium smegmatis)

"Polymerase," as used herein, refers to any natural, or non-naturally occurring enzyme or other catalyst that is capable of catalyzing a polymerization reaction, such as the polymerization of nucleotide monomers to form a nucleic acid polymer. Exemplary polymerases that may be used in the compositions and methods of the present disclosure include the nucleic acid polymerases such as DNA polymerase (e.g., enzyme of class EC 2.7.7.7), RNA polymerase (e.g., enzyme of class EC 2.7.7.6 or EC 2.7.7.48), reverse transcriptase (e.g., enzyme of class EC 2.7.7.49), and DNA ligase (e.g., enzyme of class EC 6.5.1.1) as well as terminal deoxyrobonucleotidyl transferase (EC 2.7.7.31) and DNA helicase (EC 3.6.4.1).

"Nucleic acid," as used herein, generally refers to a molecule of one or more nucleic acid subunits which comprise one of the nucleobases, adenine (A), cytosine (C), guanine (G), thymine (T), and uracil (U), or variants thereof. Nucleic acid can refer to a polymer of nucleotides (e.g., dAMP, dCMP, dGMP, dTMP), also referred to as a polynucleotide or oligonucleotide, and includes DNA, RNA, in both single and double-stranded form, and hybrids thereof.

"Naturally occurring" or "wild-type" refers to the form found in nature. For example, a naturally occurring or wild-type protein is a protein having a sequence present in an organism that can be isolated from a source found in nature, and which has not been intentionally modified by human manipulation.

"Recombinant" or "engineered" or "non-naturally occurring" when used with reference to, e.g., a cell, nucleic acid, or polypeptide, refers to a material that has been modified in a manner that would not otherwise exist in nature, or is identical thereto but produced or derived from synthetic materials and/or by manipulation using recombinant techniques. Non-limiting examples include, among others, recombinant cells expressing genes that are not found within the native (non-recombinant) form of the cell or express native genes that are otherwise expressed at a different level.

"Nanopore," as used herein, refers to a pore, channel, or passage formed or otherwise provided in a membrane or other barrier material that has a characteristic width or diameter of about 0.1 nm to about 1000 nm. A nanopore can be made of a naturally-occurring pore-forming protein, such as α-hemolysin from S. aureus, or a mutant or variant of a wild-type pore-forming protein, either non-naturally occurring (i.e., engineered) such as α-HL-C46, or naturally occurring. A membrane may be an organic membrane, such as a lipid bilayer, or a synthetic membrane made of a non-naturally occurring polymeric material. The nanopore may be disposed adjacent or in proximity to a sensor, a sensing circuit, or an electrode coupled to a sensing circuit, such as, for example, a complementary metal-oxide semiconductor (CMOS) or field effect transistor (FET) circuit.

"Linker," as used herein, refers to any molecular moiety that provides a bonding attachment with some space between two or more molecules, molecular groups, and/or molecular moieties. Exemplary linkers that may be used in the compositions and methods of the present disclosure can include polymeric chains of two to 100 polyethylene glycol (PEG) moieties, which polymeric chains can further include alkyl, alkene, alkyne, ester, ether, amide, imide, and/or phosphodiester groups.

"Solid substrate," or "solid support," as used herein refers to any solid phase material to which a biomolecule can be attached. Exemplary solid-substrates that may be used with the compositions and methods of the present disclosure include beads, slides, wells, chips, made of various solid-phase materials including glass, polymer, and silicon.

Detailed Description Of Embodiments

The inverse electron demand Diels-Alder (IEDDA) reaction based on the efficient coupling of tetrazine with trans-cyclooctene was published in 2008 (see e.g., Blackman et al. (2008)). Since then, the IEDDA conjugation chemistry has been applied to labeling proteins with rare isotope labels and other small molecules. (See e.g., Reiner et al. (2014); US 2013/0266512 A1; US 2013/0085271 A1).

The IEDDA reaction as disclosed herein for the preparation of a conjugate between a pore-forming protein, such as α-hemolysin, and a biomolecule, such as DNA polymerase, generally requires precursor reagents comprising the tetrasine ("TZ") moiety attached to either the pore-forming protein or the biomolecule, and the trans-cyclooctene ("TCO") moiety attached to the other. It is the TZ and TCO moieties that undergo the IEDDA reaction resulting in conjugation of the pore-forming protein and the biomolecule. Thus, the general reaction between TCO- and TZ-precursor reagents to provide the conjugate compositions of the present disclosure is shown in Scheme 1.

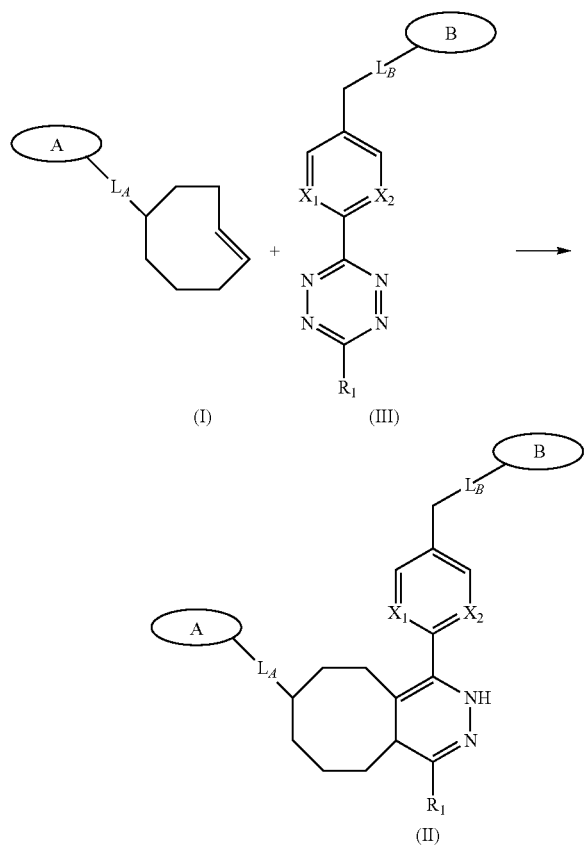

Scheme 1

As presented in Scheme 1, one of A and B is a pore-forming protein, and the other is a biomolecule, and $L_A$ and $L_B$ are linkers that provide a covalent coupling between the TCO and TZ moieties and the pore-forming protein or biomolecule.

The compositions and methods of preparation based on the IEDDA of Scheme 1 disclosed herein, can be used with a wide range of pore-forming proteins, in both naturally-occurring, and non-naturally occurring (e.g., engineered or recombinant) forms of the protein. A wide range of pore-forming proteins are known in the art, and the IEDDA-based conjugation reagents and methods provided herein should be broadly applicable to them due to their common amino acid polymeric structure. Accordingly, in some embodiments of the present disclosure, the pore-forming protein used in the compositions and methods based on Scheme 1 are selected from the group consisting of α-hemolysin, β-hemolysin, γ-hemolysin, aerolysin, cytolysin, leukocidin, melittin, MspA porin and porin A.

It is a surprising advantage of the compositions and methods of preparation based on IEDDA of Scheme 1 disclosure herein that conjugate compositions of formula (I) form quickly and efficiently wherein both the pore-forming protein and the biomolecule are large proteins, and accordingly only available in the reaction solution in relatively low concentrations. For example, in some embodiments of the methods of preparation of the conjugate compositions of formula (I), the pore-forming protein and/or the biomolecule are present in the reaction solution at a concentration of less than 1000 µM, 750 µM, 500 µM, 250 µM, 100 µM, 50 µM, 10 µM, 5 µM, or 1 µM or less.

Because the quick and efficient IEDDA reaction of Scheme 1 allows for such low reactant concentrations, the compositions and methods of preparation pore-forming proteins and biomolecules can be made in much higher weight ranges. Thus, in some embodiments of the compositions and methods of preparation disclosed herein, the pore-forming protein has a molecular weight of at least 20 kDa, 30 kDa, 40 kDa, 50 kDa, or greater. In some embodiment of the composition, the biomolecule has a molecular weight of at least 30 kDa, 40 kDa, 50 kDa, 60 kDa, 70 kDa, 80 kDa, or greater. In some embodiments, the pore-forming protein has a molecular weight of at least 30 kDa and the biomolecule has a molecular weight of at least 50 kDa.

Moreover, the IEDDA reaction of the Scheme 1 has the surprising advantage of allowing for the formation of conjugates of formula (I) wherein the pore-forming protein is part of a large multimeric protein complex. Accordingly, in some embodiments of the compositions and methods of preparation disclosed herein, the pore-forming protein is a part of a multimeric complex, wherein the multimer is selected from hexamer, heptamer, octamer, nonamer, decamer, or larger multimer. In some embodiments, the pore-forming protein is a single monomer which is part of a multimeric complex, wherein the other monomers of the complex do not comprise a composition of formula (I) (i.e., only a single monomer of the multimer is conjugated to the biomolecule).

In one embodiment, the pore-forming protein comprises α-hemolysin from *Staphylococcus aureus* (also referred to herein as "α-HL"). α-HL is one of the most-studied members of the class of pore-forming proteins, and has been sequenced, cloned, extensively characterized structurally and functionally using a wide range of techniques including site-directed mutagenesis and chemical labelling (see e.g., Valeva et al. (2001), and references cited therein). In particular, α-HL has had cysteine residue substitutions inserted at numerous positions allowing for covalent modification of the protein through maleimide linker chemistry (Ibid.) In some embodiments, the α-hemolysin useful in the methods of the present disclosure can be a non-naturally occurring engineered pore-forming protein α-hemolysin-C46 ("α-HL-C46"), which comprises α-hemolysin from *S. aureus* with a K46C amino acid residue substitution.

Generally, the pore-forming proteins useful in the embodiments of the present disclosure are capable of spontaneously self-assembling nanopores in membranes, wherein the nanopore has a diameter in a range from about 0.5 nanometer to about 25 nanometers. In some embodiments of the compositions and methods disclosed herein, the pore-forming protein is embedded in a membrane, and thereby forming a nanopore through the membrane (or other barrier material). Accordingly, in some embodiments, the pore-forming protein is a nanopore, and/or is part of a multimeric protein complex or assembly that forms a nanopore.

Where the pore-forming protein is α-HL, a heptameric complex of the α-HL monomers can spontaneously form a nanopore in a lipid bilayer. It has been shown that heptamers of α-HL comprising a ratio of 6:1 native α-HL to mutant α-HL can form nanopores (see e.g., Valeva et al. (2001), and references cited therein). Accordingly, in some embodiments, the compositions and methods of the present disclosure can comprise a nanopore, wherein the nanopore comprises a heptameric α-HL complex, which has 6:1 native α-HL to α-HL-C46, and further wherein the α-HL-G46 is conjugated to a biomolecule as in Scheme 1. In some embodiments, the biomolecule conjugated to the nanopore is a DNA polymerase.

Further it is contemplated that the compositions and methods of preparation based on Scheme 1 disclosed herein, can comprise carrying out the IEDDA reaction using a TZ- or TCO-modified pore-forming protein, wherein the pore-forming protein is part of a multimeric complex that has formed a nanopore. Thus, in some embodiments, the method of forming the conjugate comprises first forming a nanopore comprising a pore-forming protein that is modified with either TZ or TCO, and then carrying out an IEDDA reaction between this TZ- or TCO-modified nanopore with the complementary TCO- or TZ-modified biomolecule. Accordingly, in some embodiments, the present disclosure provides a composition comprising a heptameric α-HL nanopore, wherein at least one of the α-HL monomer units is covalently linked to a TZ-moiety or a TCO-moiety. In some embodiments, the heptameric α-HL nanopore comprises 6 native α-HL monomers and 1 α-HL mutant monomer that comprises an amino acid residue covalently linked to a TZ-moiety or a TCO-moiety. In some embodiments, the 1 α-HL mutant monomer is α-HL-C46. In some embodiments, the 1 α-HL-C46 monomer is covalently linked to either a TCO or a 6-Me-TZ moiety.

In some embodiments, it is contemplated that the IEDDA reaction of Scheme 1 can be carried out wherein the pore-forming protein is part of a nanopore that is in solution. However, it is also contemplated that in some embodiments the reaction of Scheme 1 are carried out wherein the pore-forming protein is part of a nanopore that is immobilized, such as through covalent or non-covalent attachment (directly or indirectly) to a solid support.

It is contemplated that the nanopores comprising the pore-forming protein conjugate compositions of the present disclosure can be used in typical nanopore applications and devices, such as single-molecule nucleic acid sequencing. Nanopore devices and methods for making and using them are disclosed in e.g., U.S. Pat. Nos. 7,005,264 B2; 7,846,738; 6,617,113; 6,746,534; 6,673,615; 6,627,067; 6,464,842; 6,362,002; 6,267,872; 6,015,714; 5,795,732 and U.S. Publication Nos. 2013/0264207, 2013/0244340, 2004/0121525, and 2003/0104428, each of which are hereby incorporated by reference in their entirety. In such nanopore embodiments, the pore-forming protein typically is embedded in a membrane attached to a solid substrate. Typically, the solid substrate comprises a material selected from the group consisting of polymer, glass, silicon, and a combination thereof. Additionally, the solid substrate can further comprise adjacent to the nanopore, a sensor, a sensing circuit, or an electrode coupled to a sensing circuit, optionally, a complementary metal-oxide semiconductor (CMOS), or field effect transistor (FET) circuit.

Generally, biomolecules useful in the embodiments of the present disclosure can be any protein or nucleic acid that might be desirable to conjugate with a pore-forming protein, and thereby position adjacent to a nanopore, and accompanying nanopore detection system. In one embodiment it is contemplated that the conjugate compositions of the present disclosure can be used in nanopore-based nucleic acid sequencing devices. Accordingly, in some embodiments of the compositions and methods disclosed herein, the biomolecule is an enzyme capable of catalyzing the synthesis of a nucleotide polymer. In some embodiments, the biomolecule is an enzyme selected from the group consisting of a DNA polymerase, RNA polymerase, reverse transcriptase, terminal transferase, helicase, and DNA ligase. In some embodiments, the biomolecule is a naturally-occurring or non-naturally occurring (e.g., engineered) enzyme that has 5'→3' DNA polymerase activity and strong strand displacement activity but lacks exonuclease activity.

A wide range of polymerases and ligases are known in the art, and the IEDDA-based conjugation reagents and methods provided herein should be broadly applicable to them due to their common amino acid polymeric structure. Exemplary polymerases that may be used in the compositions and methods of the present disclosure include the nucleic acid polymerases such as DNA polymerase (e.g., enzyme of class EC 2.7.7.7), RNA polymerase (e.g., enzyme of class EC 2.7.7.6 or EC 2.7.7.48), reverse transcriptase (e.g., enzyme of class EC 2.7.7.48), and DNA ligase (e.g., enzyme of class EC 6.5.1.1). In some embodiments, the biomolecule comprises a DNA polymerase from *Bacillus stearothermophilus*. In some embodiments, the biomolecule comprises the large fragment of DNA polymerase from *B. stearothermophilus*. In one embodiment, the biomolecule is DNA polymerase Bst 2.0 (commercially available from New England BioLabs, Inc., Massachusetts, USA). In some embodiments, the biomolecule is 9°polymerase, *E. Coli* DNA Polymerase I, Bacteriophage T4 DNA polymerase, Sequenase, Taq DNA polymerase, 9°N polymerase (exo-)A485L/Y409V or Phi29 DNA polymerase (φ29 DNA Polymerase).

In the embodiments of the disclosure, it is not critical whether the pore-forming protein is attached to the TZ moiety or TCO moiety. In the IEDDA reaction as discussed herein, however, the ratio of the TZ to the TCO precursor reagent, is from about 1.1 to 5, and in some embodiments, optimal reactivity is achieved with a 3-fold excess of the TZ reagent. In some embodiments, it may be preferred for the pore-forming protein to be linked to TZ and the biomolecule to the TCO in the reaction of Scheme 1.

Methods of attaching IEDDA reactive groups of Scheme 1, such as TZ or TCO moieties, to pore-forming proteins or biomolecules, are well-known in the art, and several are provided by the present disclosure and Examples herein. Generally, the TZ- or TCO-moiety can be attached to (or commercially obtained attached to) a linker (e.g., a linear chain of polyethylene glycol groups) with a distal maleimide or NHS group. The maleimide and NHS groups form facile covalent cross-links to cysteine and lysine residues, respectively. Thus, as is well-known in the art of protein cross-linking, one may use standard protein engineering techniques to generate a mutant version of the desired pore-forming protein or biomolecule such that provides a cysteine or lysine residue available for cross-linking to the TZ- or TCO-moiety. For example, the present disclosure provides an α-HL mutant with a single cysteine residue (α-HL-C46) and a commercially available DNA polymerase with an available cysteine (Bst2.0). It is contemplated that in some embodiments, other pore-forming proteins and/or biomolecules can be modified to allow for facile attachment of the TZ- or TCO-moiety through a linker and known protein cross-linking chemistry.

A wide range of TZ reagents known in the art are capable of undergoing the IEDDA reaction with a TCO reagent. (See e.g., US 2010/0016545 A1; US2013/0266512 A1; US 2013/0085271 A1.) The present disclosure provides a range of TZ reagents based on the variable groups $X_1$, $X_2$, and $R_1$ included in the compound of formulas (II) and (III) of Scheme 1. Thus, $X_1$ and $X_2$ can be atoms independently selected from C and N; and $R_1$ is a chemical group that can be selected from the group consisting of: H, F, Cl, Br, I, $CH_3$, $CF_3$, $NH_2$, $NO_2$, OH, C(O)OH, C(O)OCH$_3$, C(O)NH$_2$, linear or branched ($C_2$-$C_5$) alkyl, linear or branched ($C_2$-$C_5$) alkenyl, linear or branched ($C_2$-$C_5$)alkynyl, unsubstituted or para-substituted 6-membered aryl ring, and unsubstituted or para-substituted 6-membered heteroaryl ring.

In some embodiments of the TZ reagent compound of formula (II) disclosed herein, the $X_1$ and $X_2$ atoms are each C, and $R_1$ is a $CH_3$ group. In other embodiments, one or both of the $X_1$ and $X_2$ atoms are N. With regard to the $R_1$ substituent, various embodiments provide for a wide range of possible groups at the position. Thus, in some embodiments, $R_1$ is an unsubstituted or para-substituted 6-membered aryl ring, or an unsubstituted or para-substituted 6-membered heteroaryl ring selected from the group consisting of: phenyl, benzoic acid, 4-methyl-phenyl, 4-methoxy-phenyl, 4-trifluoromethyl-phenyl, 2-pyridyl, 2-pyridyl-4-methyl, 2-pyridyl-4-carboxylic acid, 2-pyrimidyl, 2-pyrimidyl-4-methyl, and 2-pyrimidyl-4-carboxylic acid.

In more specific embodiments, the TZ reagent compound of formula (II) can be any of the compounds of formula (IIa) to formula (IIn):

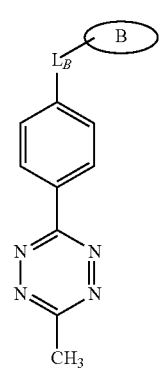
(IIa)

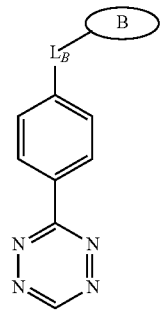
(IIb)

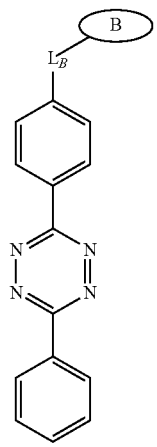
(IIc)

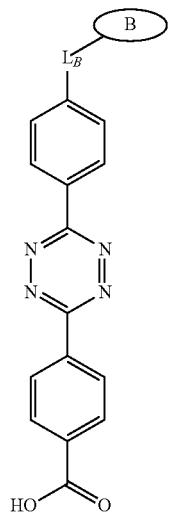
(IId)

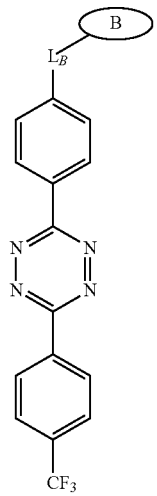
(IIe)

(IIf)
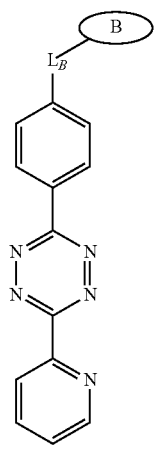
(IIg)
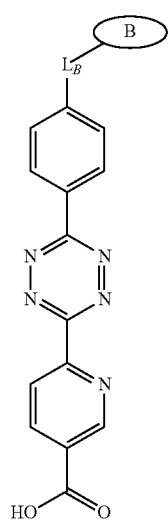
(IIh)
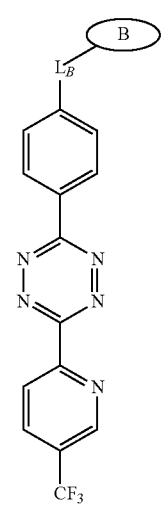
(IIi)
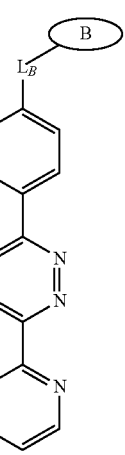
(IIj)
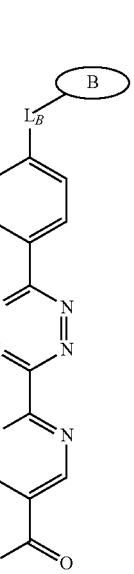
(IIk)
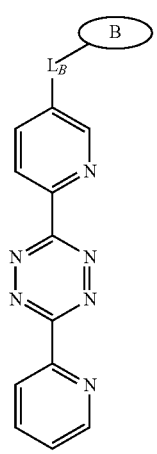

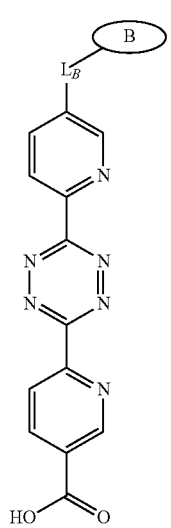

(IIm)

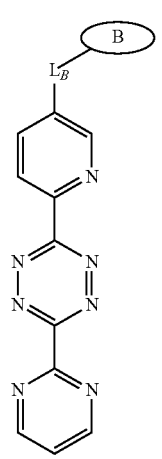

(IIn)

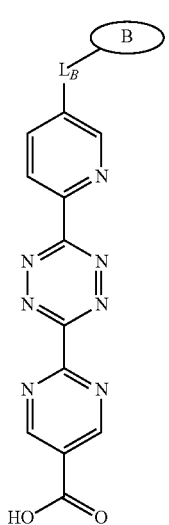

With regard to the TCO reagent, the ring strain created by the trans-conformation contributes to the driving force for the IEDDA reaction with the TZ moiety on the other reagent. The present disclosure provides some variability in the attachment to the linker moiety to the trans-cyclooctene. In some embodiments, the TCO reagent compound of formula (III) can be any of the compounds of formula (IIIa) to formula (IIIc):

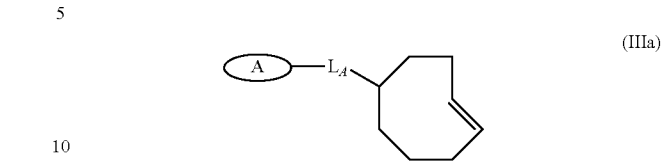

(IIIa)

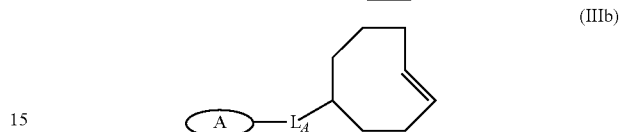

(IIIb)

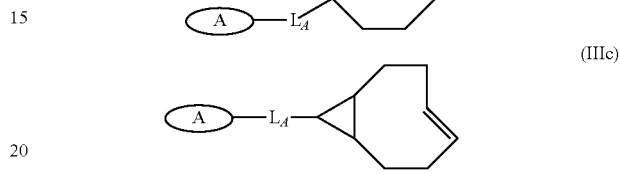

(IIIc)

Based on the general reaction of Scheme 1, the present disclosure provides a method of preparing a composition comprising a pore-forming protein conjugate compound of formula (I), wherein the method comprises contacting under suitable reaction conditions: (a) a testrazine-linker-conjugate compound of formula (II)

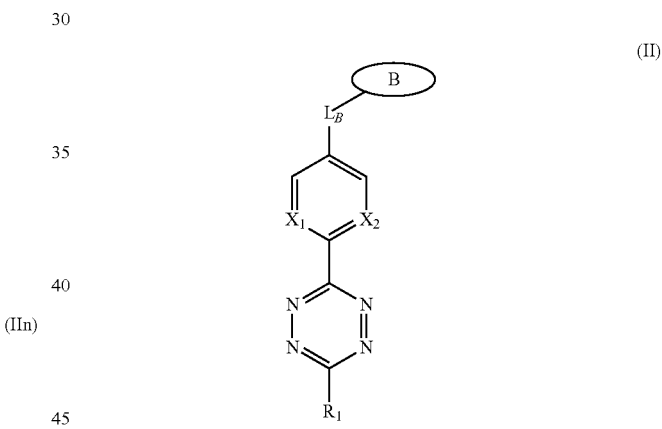

(II)

and (b) a TCO-linker-conjugate compound of formula (III),

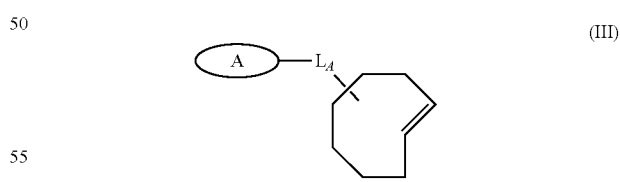

(III)

wherein, one of A and B is a pore-forming protein, and the other is a biomolecule capable of catalyzing the synthesis of a nucleotide polymer; $L_A$ and $L_B$ are linkers; $X_1$ and $X_2$ are atoms independently selected from C and N; and $R_1$ is a chemical group selected from the group consisting of: H, F, Cl, Br, I, $CH_3$, $NH_2$, $NO_2$, OH, C(O)OH, C(O)OCH$_3$, C(O)NH$_2$, linear or branched ($C_2$-$C_5$) alkyl, linear or branched ($C_2$-$C_5$) alkenyl, linear or branched ($C_2$-$C_5$) alkynyl, unsubstituted or para-substituted 6-membered aryl ring, and unsubstituted or para-substituted 6-membered heteroaryl ring; and whereby the contacted, compounds of formula (II) and formula (III) undergo an inverse electron demand Diels-Alder (IEDDA) reaction to form a conjugate of the pore-forming protein and the biomolecule. In some embodiments of this method the TZ-reagent comprises a compound of any one of formula (IIa) through (IIn) and the TCO-reagent comprises a compound of any one of formulas (IIIa) through (IIIc).

Based on the range of TZ-reagent compounds of formula (IIa) through formula (IIn) provided herein, a similar range of pore-forming protein conjugate compositions can be obtained using the IEDDA reaction of Scheme 1. Thus, the present disclosure provides compositions comprising a pore-forming protein conjugate compound of formula selected from the group consisting of formula (Ia) through formula (In):

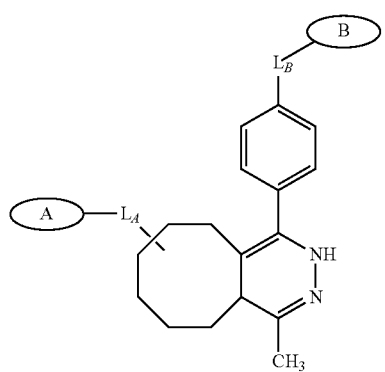
(Ia)

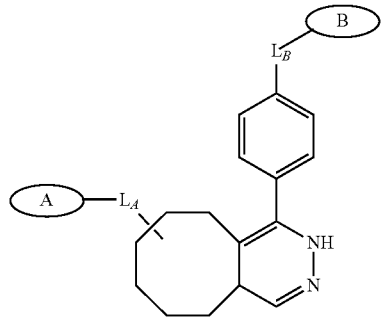
(Ib)

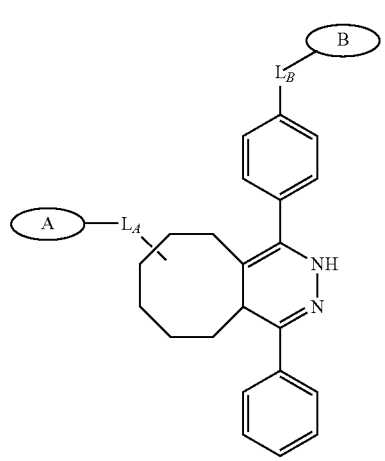
(Ic)

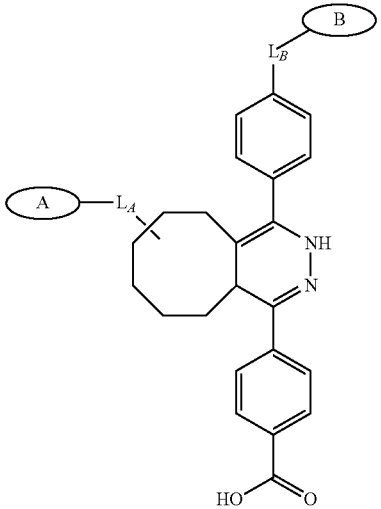
(Id)

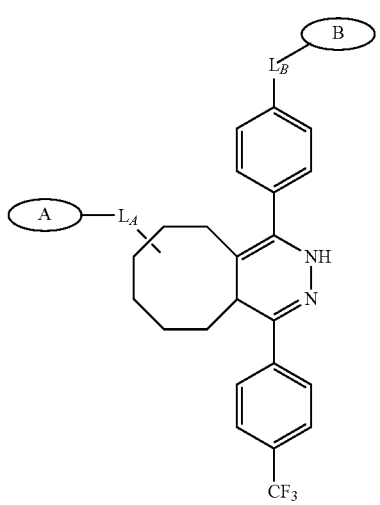
(Ie)

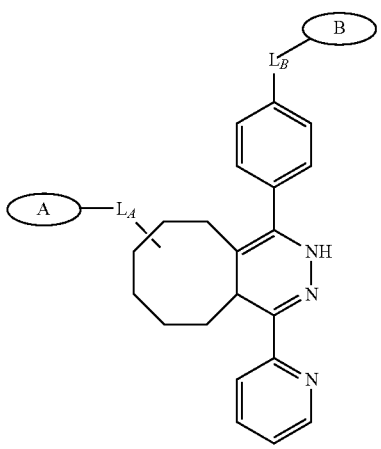
(If)

(Ig)
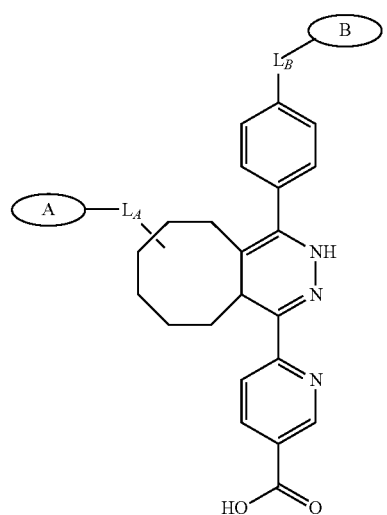
(Ih)
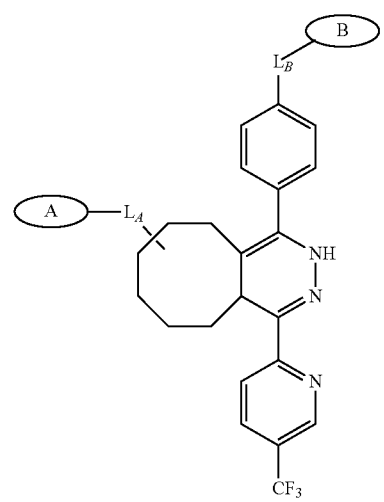
(Ii)
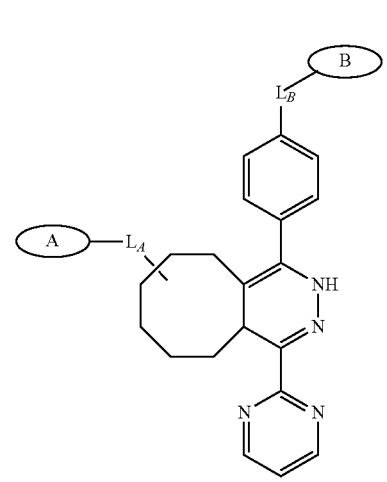
(Ij)
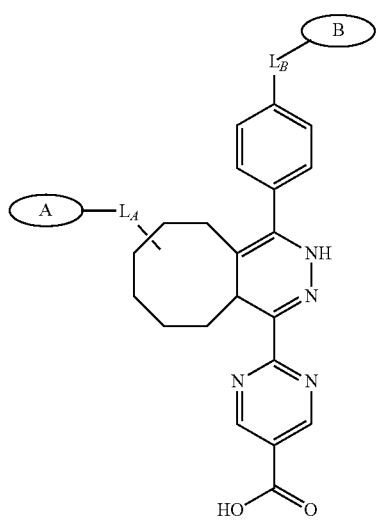
(Ik)
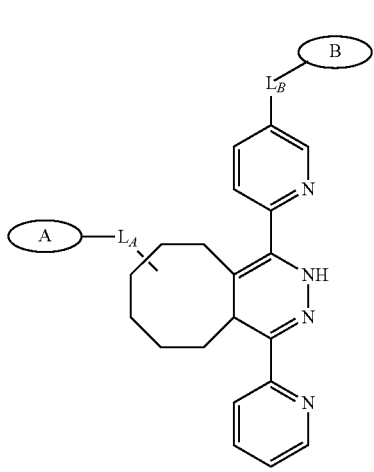
(Il)
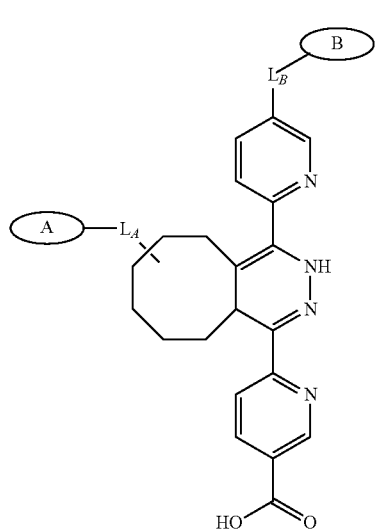

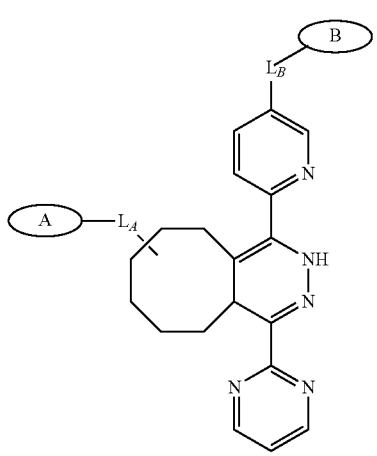
(Im)

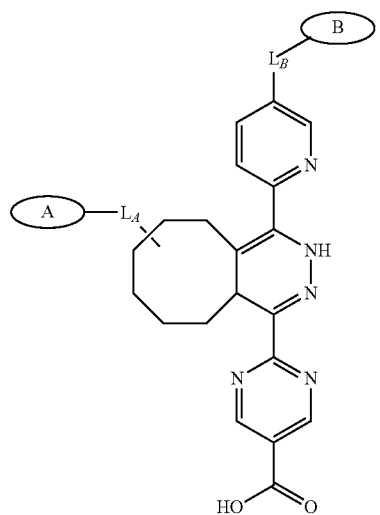
(In)

Similarly, based on the range of TCO-reagent compounds of formula (IIIa) through formula (IIIc) provided herein, a similar range of pore-forming protein conjugate compositions can be obtained using the IEDDA reaction of Scheme 1. Thus, the present disclosure provides compositions comprising a pore-forming protein conjugate compound of formula selected from the group consisting of formula (Io) through formula (Iq), wherein the variable groups $X_1$, $X_2$, and $R_1$ can be any of those described above for the TZ-reagent:

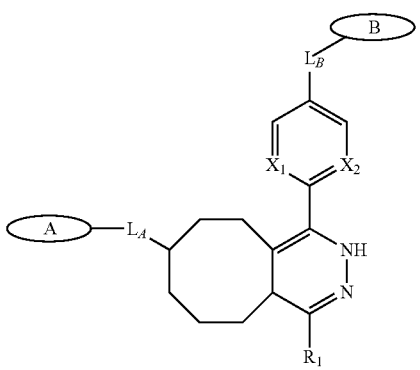
(Io)

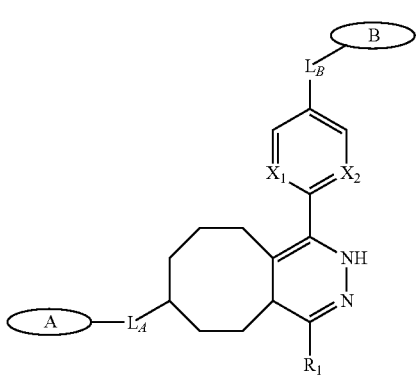
(Ip)

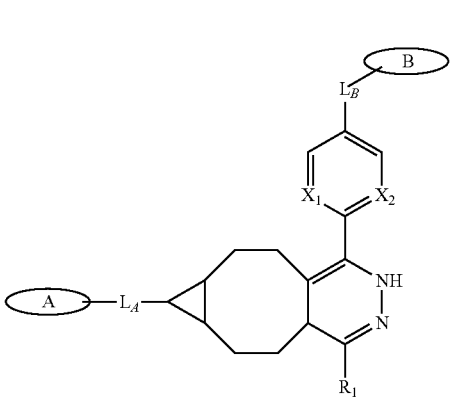
(Iq)

The linker groups, $L_A$ and $L_B$ used in the TZ-reagent and TCO-reagent compounds of formulas (II) and (III), generally can include any of the linker (or spacer) moieties that are capable of providing a covalent link and desired space between the pore-forming protein and biomolecule. Such linker moieties are well-known and commercially available for use in conjugating or cross-linking proteins or other biomolecules. (See e.g., catalog of "crosslinking reagents" available from Thermo Scientific, USA at www.piercenet-.com or Sigma-Aldrich, USA at www.sigmaaldrich.com).

Accordingly, in general embodiments of the present disclosure, the linker groups, $L_A$ and $L_B$ useful in the compounds of formula (II) and (III) for carrying out the IBDDA reaction of Scheme 1 can include a covalently bonded chain of 2 to 100 atoms comprising one or more of the following chemical groups: linear ($C_1$-$C_5$) alkyl, linear ($C_1$-$C_5$) alkene, linear ($C_1$-$C_5$) alkyne, ester, ether, amine, amide, imide, phosphodiester, and/or polyethylene glycol (PEG). PEG linkers are well-known for use in conjugating biomolecules. Accordingly, in certain embodiments of the compositions of the present disclosure, the linkers $L_A$ and $L_B$ comprise a polymer of from 1 to 50 PEG moieties, in some embodiments, a polymer of from 2 to 25 PEG moieties, and in some embodiments, a polymer of from 2 to 15 PEG moieties.

Generally, the reagents used to prepare the linkers in the compounds of formula (II) and (III) comprise a group that allows for facile reaction and covalent attachment of the linker to the pore-forming protein or biomolecule through an available sulfhydryl or primary amine group. Typically, the reactive linker group is a maleimide group or an N-succinimide ester (NHS) group. Accordingly, in some embodiments of the compositions formulas (II), (III), and (I), of Scheme 1, the linkers $L_A$ and $L_B$ attach to A and B (i.e., the pore-forming protein and biomolecule) either through a thioether bond to a sulfhydryl group on A and/or B, or through a peptide bond to a primary amine group of A and/or B.

TCO-linker-maleimide and TCO-linker-NHS-ester reagents are commercially available wherein the linker comprises a polymer of 3 PEG moieties (Jena Bioscience GmbH, Jena Germany). Also commercially available are TZ-linker-maleimide and TZ-linker-NHS ester reagents, wherein the TZ moiety is 6-methyl tetrazine and the linker comprises a polymer of 4 or 5 PEG moieties (Jena Bioscience GmbH, Jena, Germany). These commercially available maleimide reagents have been used to prepare a pore-forming protein conjugate with a DNA polymerase as described in Example 1 herein.

In specific embodiments, the present disclosure provides compositions of compounds of formula (I), (II), and (III), useful in the IEDDA reaction of Scheme 1, wherein the linkers $L_A$ and $L_B$ are independently selected from the group consisting of structures of formula (IVa)-formula (IVd):

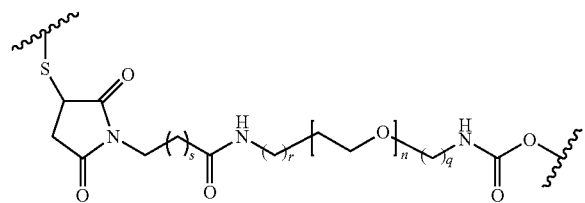

(IVa)

wherein, n=1 to 50, and q, r, and s each independently=0, 1, 2, or 3;

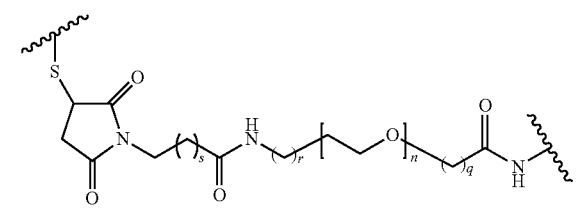

(IVb)

wherein, n=1 to 50, and q, r, and s each independently=0, 1, 2, or 3;

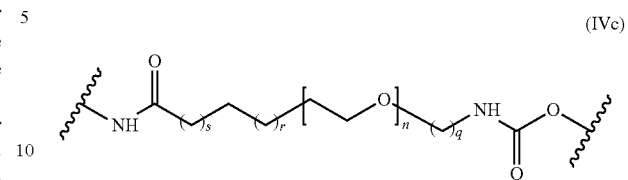

(IVc)

wherein, n=1 to 50, and q, r, and s each independently=0, 1, 2, or 3;

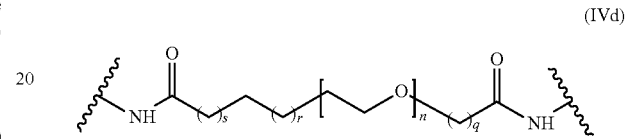

(IVd)

wherein, n=1 to 50, and q, r, and s each independently=0, 1, 2, or 3.

As suggested above, the TZ and TCO reagent compounds used in the IEDDA reaction of Scheme 1 can be prepared by reacting a TZ-linker-maleimide compound, or a TCO-linker-maleimide compound with an available sulfhydryl group (e.g., a cysteine residue) on the pore-forming protein or biomolecule. Alternatively, the TZ and TCO reagent compounds used in the IEDDA reaction of Scheme 1 can be prepared by reacting a TZ-linker-NHS compound, or a TCO-linker-NHS compound with an available amine group (e.g., a lysine residue) on the pore-forming protein or biomolecule.

In specific embodiments provided by the present disclosure, the TZ-reagent compound of formula (II) can be prepared by contacting, under suitable reaction conditions, a pore-forming protein (e.g., α-hemolysin) or biomolecule (e.g., DNA polymerase) with the TZ-linker-maleimide compound of formula (V):

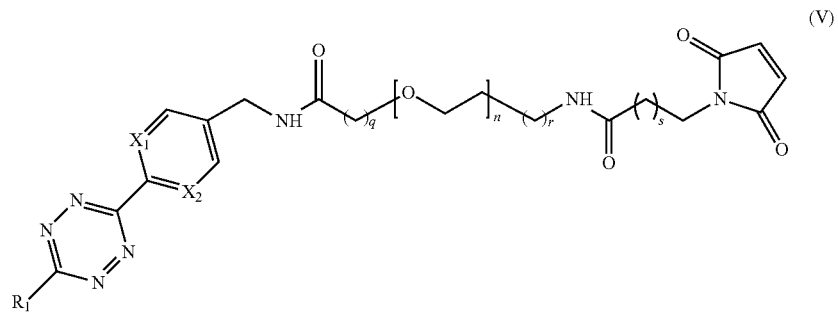

(V)

wherein, $X_1$ and $X_2$ are atoms independently selected from C and N; $R_1$ is a chemical group selected from the group consisting of: H, F, Cl, Br, I, $CH_3$, $CF_3$, $NH_2$, $NO_2$, OH, C(O)OH, C(O)$OCH_3$, C(O)$NH_2$, linear or branched ($C_2$-$C_5$) alkyl, linear or branched ($C_2$-$C_5$) alkenyl, linear or branched ($C_2$-$C_5$) alkynyl, unsubstituted or para-substituted 6-membered membered aryl ring, and unsubstituted or para-substituted 6-membered heteroaryl ring; and n=1 to 50, and q, r, and s each independently=0, 1, 2 or 3; and thereby forming a tetrazine-linker-conjugate with the pore-forming protein or biomolecule.

Similarly, in specific embodiments provided by the present disclosure, the TCO-reagent compound of formula (III) can be prepared by contacting, under suitable reaction conditions, a pore-forming protein (e.g., α-hemolysin) or biomolecule (e.g., DNA polymerase) with the TCO-linker-maleimide compound of formula (VI):

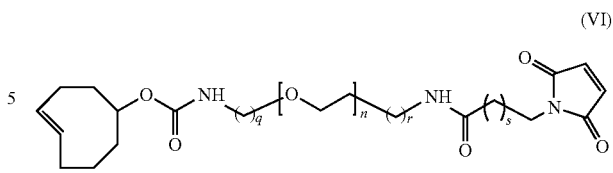

wherein, n=1 to 50, and q, r, and s each independently=0, 1, 2 or 3; and thereby forming a TCO-linker-conjugate with the pore-forming protein or biomolecule.

In a specific embodiment, the IEDDA reaction of Scheme 1 can be carried out using a TZ-reagent compound comprising a TZ-moiety of formula (IIa) and a linker structure of formula (IVb) and a TCO-reagent compound comprising a TCO-moiety of formula (Io) and a linker structure of formula (IVa), resulting a pore-forming protein conjugate compound of formula (Ir):

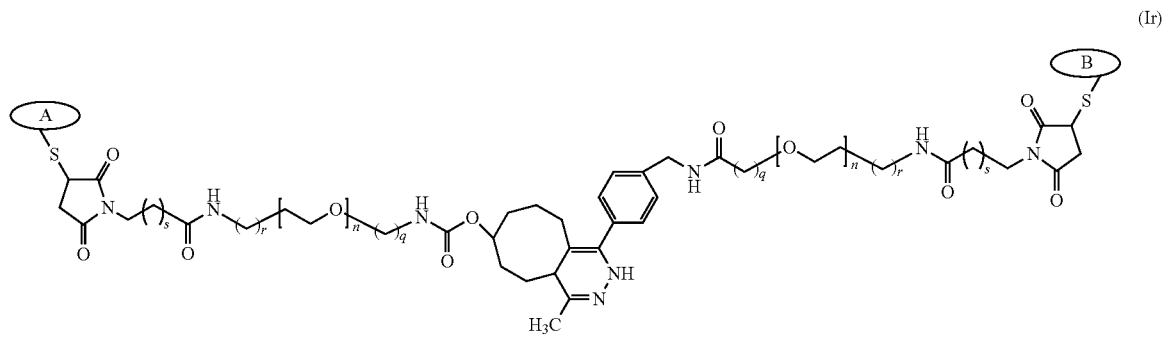

wherein, n=1 to 50, and q, r, and s each independently=0, 1, 2 or 3.

In another specific embodiment, the IEDDA reaction of Scheme 1 can be carried out using a TZ-reagent compound comprising a TZ-moiety of formula (IIa) and a linker structure of formula (IVd) and a TCO-reagent compound comprising a TCO-moiety of formula (Io) and a linker structure of formula (IVc), resulting a pore-forming protein conjugate compound of formula (Is):

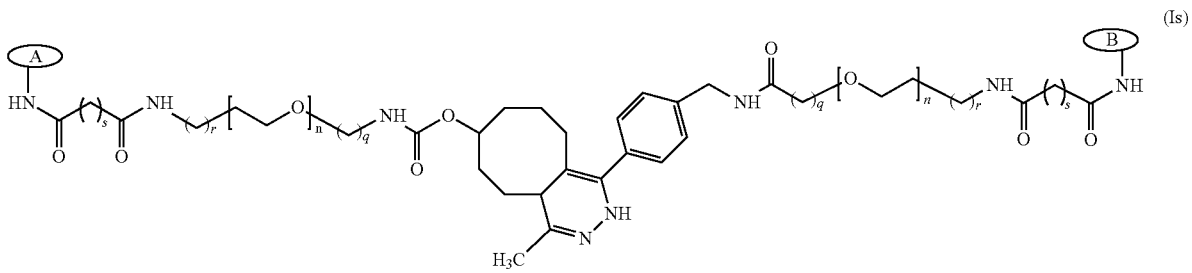

wherein, n=1 to 50, and q, r, and s each independently=0, 1, 2 or 3.

In a specific embodiment of the present disclosure, the IEDDA reaction of Scheme I can be carried out wherein the tetrazine-linker-conjugate compound of formula (II) is a compound of formula (IIp):

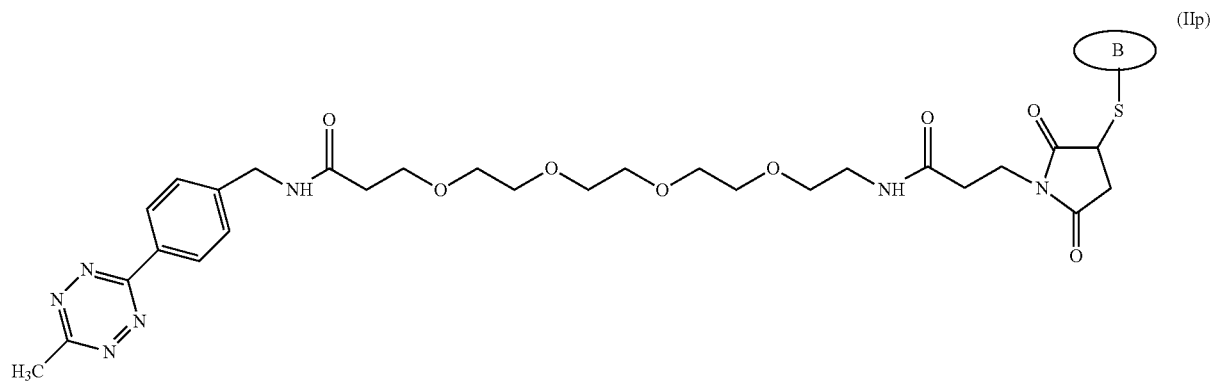

and the TCO-linker-conjugate compound of formula (III) is a compound of formula (IIIe):

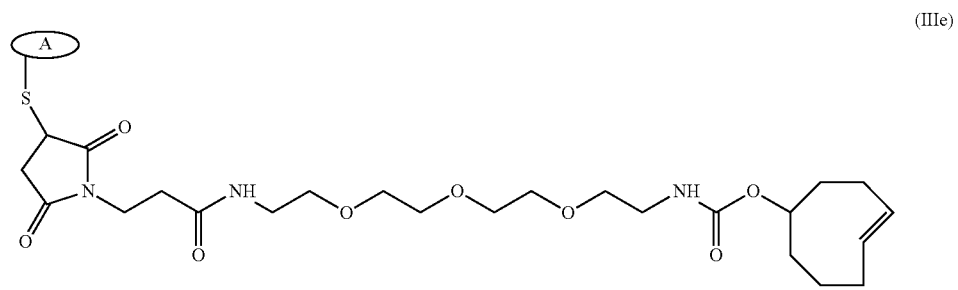

In this embodiment, the resulting pore-forming protein conjugate composition of formula (I) comprises a compound of formula (It):

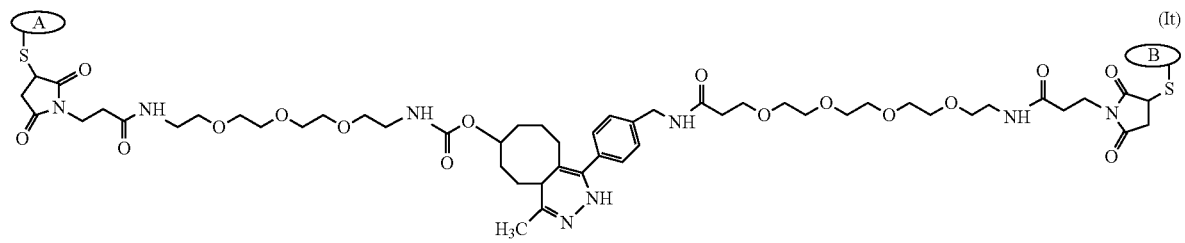

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1

Preparation of a Pore-Polymerase Conjugate Composition

This example illustrates the use of a fast IEDDA "click" reaction of 6-methyl-tetrazine ("6-Me-TZ") and trans-cyclooctene ("TCO") maleimide linker reagents to prepare a composition of a pore-forming protein (α-hemolysin) conjugated with an enzyme (DNA polymerase Bst 2.0).

Briefly, the general method of preparation of the conjugate included the steps of preparing a heptameric complex of α-hemolysin ("α-HL") wherein one of the seven monomer units was the α-HL-C46 mutant. α-HL-C46 has the naturally occurring lysine at position 46 substituted with a cysteine and an N-terminal 6-His tag for purification. The presence of the cysteine in this α-HL-C46 mutant monomer unit allows for the attachment of a single TCO-maleimide linker reagent to the heptameric pore complex. This TCO-group can then conjugate via an IEDDA click reaction with a TZ-group on a modified DNA polymerase. In this example, the single naturally-occurring cysteine residue of DNA polymerase Bst 2.0 was modified with a 6-Me-TZ-maleimide reagent. This 6-Me-TZ-Bst 2.0 adduct was then combined with the TCO-α-HL adduct in a 10:1 ratio to provide a α-HL heptamer conjugate with polymerase Bst 2.0 enzyme. Materials and methods for the modification α-HL-C46 with maleimide linker reagents, and the formation of heptameric α-hemolysin pores incorporating α-HL-C46 also are described in e.g., Valeva et al. (2001), and references cited therein.

Preparation of 6:1 α-HL:α-HL-C46 heptameric pore complex: The K46C (lysine at position 46 substituted with cysteine) mutant of a S. aureus α-HL monomer with a 6-His tag ("α-HL-C46") was prepared using standard protein engineering techniques. (see e.g., Valeva et al. (2001) and Palmer et al. (1993)) The α-RL-C46 was purified as described in the protocol for "PrepEase" His-tagged protein purification kits (USB-Affymetrix; USA) and exchanged into 1×PBS with 1 mM tris-carboxyethyl-phosphine (TCEP) at pH 7.2 at 1.0 mg/mL protein concentration. This purified α-HL-C46 was mixed with wild-type α-HL in the presence of lipid to form heptamers as follows. To obtain a heptameric pore complex with the optimal 6:1 ratio of native α-HL monomers to the α-HL-C46 mutant monomer, an 11:1 ratio was used for oligomerization. Lipid (1,2-diphytanoyl-sn-glycero-3-phosphocholine, powder, Avanti Polar Lipids) was added to a final concentration of 5 mg/mL in 50 mM tris, 200 mM NaCl, pH 8.0 for 30 minutes at 40° C. 5% octyl-beta-glucoside (β-OG) was added to pop vesicles, as assessed by clearing, to solubilize the proteins. Then samples were concentrated using 100K MWCO filters and spun at 24000 RPM for 30 minutes to pellet the precipitated protein. After equilibrating size-exclusion columns with 30 mM βOG, 75 mM KCl, 20 mM HEPES at pH 7.5, 500 µL of the concentrated samples were loaded at low pressure to separate heptameric 6:1 α-HL pore complexes from monomers. After concentration to 5 mL in two consecutive size-exclusion columns, the samples were loaded on Mono S 5/50 GL columns (GE Healthcare; New Jersey, USA). Further FPLC was used to separate the 6:1 α-HL:α-HL-C46 pores from those having different subunit stoichiometrics (e.g., 7:0, 5:2). The mobile phase consisted of: A, running buffer: 20 mM 2-(N-morpholino) ethanesulfonic acid (MES), 0.1% Tween®20, at pH 5; B, elution buffer: 2M NaCl, 20 mM MES, 0.1% Tween®20 at pH 5. Purification was performed from 100% A isocratic over 21 minutes followed by a linear gradient of 0-100% B for 20 minutes and then 100% B isocratic over another 2 minutes. The flow rate was 1 ml/min. Pure native 7:0 α-HL heptameric pore complex eluted first and the 6:1 α-HL:α-HL-C46 heptameric pore compiexe eluted with a retention time of from about 24.5 min to about 25.5 min.

Preparation of TCO-PEG$_3$-α-HL reagent: A solution of 6:1 α-HL heptameric pore complex was exchanged into a phosphate reaction buffer (100 mM sodium phosphate, 150 mM NaCl, pH 7.2) and concentrated, using a 100K cut-off desalting spin column to ~300 µg of 6:1 α-HL pore complex in ~100 µL volume. A 50 mM TCO-PEG$_3$-maleimide (Jena Bioscience GmbH, Jena, Germany) stock solution was prepared in DMSO. The TCO-PEG$_3$-maleimide stock was added to the 6:1 α-HL pore solution (described above) resulting in a reaction, mixture having 100-fold molar excess of the maleimide reagent. This mixture was allowed to react overnight with rotation at 4° C. The resulting TCO-PEG$_3$-α-HL reagent was purified on Sephadex G-50 and used in the IEDDA click reaction with the 6-Me-TZ-PEG$_4$-Bst 2.0 polymerase reagent prepared as described below.

Preparation of 6-Me-TZ-PEG$_4$-Bst 2.0 reagent: DNA polymerase Bst 2.0 (New England Biolabs, Massachusetts, USA) in phosphate reaction buffer (100 mM sodium phosphate, 150 mM NaCl, pH 7.2) was concentrated using a 10K cut-off desalting spin column to ~580 µg in ~100 µL volume. A 50 mM stock solution of 6-Me-TZ-PEG$_4$-maleimide (Jena Bioscience GmbH, Jena, Germany) in DMSO was prepared. The 6-Me-TZ-PEG$_4$-maleimide stock solution was added to the Bst 2.0 solution to yield a reaction mixture having 100-fold excess of the maleimide reagent. Following incubation at 4° C. on a rotator overnight, 1 M DTT was added to a final concentration of 5 mM, and incubation was carried out at room temperature to quench the reaction. The resulting 6-Me-TZ-PEG$_4$-Bst 2.0 reagent was purified on Sephadex G-50 and used in the IEDDA click reaction with the TCO-PEG$_3$-α-HL reagent as described below.

IEDDA click reaction of 6-Me-TZ and TCO conjugates: The IEDDA click reaction between TCO-PEG$_3$-α-HL and 6-Me-TZ-PEG$_4$-Bst 2.0 was carried out using a 5:1 molar excess of 6-Me-TZ-PEG$_4$-Bst 2.0 reagent to the TCO-PEG$_3$-α-HL reagent. Generally, the 6-Me-TZ-PEG$_4$-Bst 2.0 solution was added with mixing to a volume of the TCO-PEG$_3$-α-HL solution to provide the desired 5:1 molar excess in 1×PBS, 5 mM EDTA, at pH 7.0. The mixture was allowed to react at room temperature with rotation for 1 h and then overnight (ON) at 4° C. Then samples from the reaction mixture was prepared for SDS-PAGE and Bioanalyzer (Agilent) analysis by spin filtering (100K) followed by purification on a Superdex 200 gel-filtration column. Heat denatured samples were prepare by heating at 95° C. for 5 min under. Further purification of the conjugates was carried out using the His-tag on the α-HL-C46 by using a Ni$^{2+}$ column (PrepEase Histidine-tagged Protein Purification Mini Kit High Yield column; Affymetrix, CA, USA). The Ni$^{2+}$ column was run according the manufacturer's protocol. The α-HL nanopore-BST 2.0 conjugate product was stored in 1× PBS buffer at 4° C. prior to further use in nanopore sequencing devices.

Azido-DBCO click reaction: An experiment also was carried using the Cu-free azido-DBCO click reaction in an attempt to form a polymerase-α-HL conjugate. The click reaction between azide and DBCO can occur without the presence of copper ion, which makes it potentially useful for click reactions with polymerase enzymes that are rapidly inactivated by copper. Analogously to the experiment using the IEDDA reaction described above, α-HL-C46 was modified with an azide linker reagent, and the DNA polymerase I Klenow fragment (Klenow) was modified with a dibenzylcyclobutyne (DBCO) linker reagent. These reagents, however, were then reacted without first forming the α-HL heptameric pore complex. The azido and DBCO click reagents were prepared analogously, to the preparation of the IEDDA reagents with Bst2.0 and α-HL-C46. Azido-PEG$_3$-maleimide (Click Chemistry Tools, Scottsdale, Ariz.) was used to modify the C46 residue of the α-HL-C46 with an azido group, N$_3$-α-HL-C46. DNA polymerase I, Klenow fragment (New England BioLabs, Massachusetts, USA) was modified at its single C584 position with DBCO-PEG-maleimide (Click Chemistry Tools, Scottsdale, Ariz.) to obtain the DBCO-modified Klenow fragment, DBCO-Klenow. Both the azide and DBCO modifications of the two proteins were verified by surface-enhanced Raman spectroscopy. The prepared DBCO-Klenow solution was added to the $N_3$-α-HL-C46 solution in 1× PBS, 0.1% Tween 20, incubated one hour at room temperature, then the mixture was slowly shaken for 3 days. The reaction mixture was concentrated through a 100 kDa spin filter and the crude product analyzed by SDS-PAGE. The gel images showed bands indicating that the click reaction mixture contained α-HL-C46 monomer (~35 kDa), a small amount (~15-20%) of α-HL-C46 dimer (~70 kDa), Klenow fragment (~75 kDa), and very small amount (<5%) of putative α-HL-C46-Klenow conjugate at ~110 kDa.

Results: Images of the SDS PAGE gel and Agilent Bioanalyzer analysis of the native, denatured, and further $Ni^{2+}$ purified samples of the reaction mixture of IEDDA reaction of FIG. 1 are shown in FIG. 2.

Figure 2:
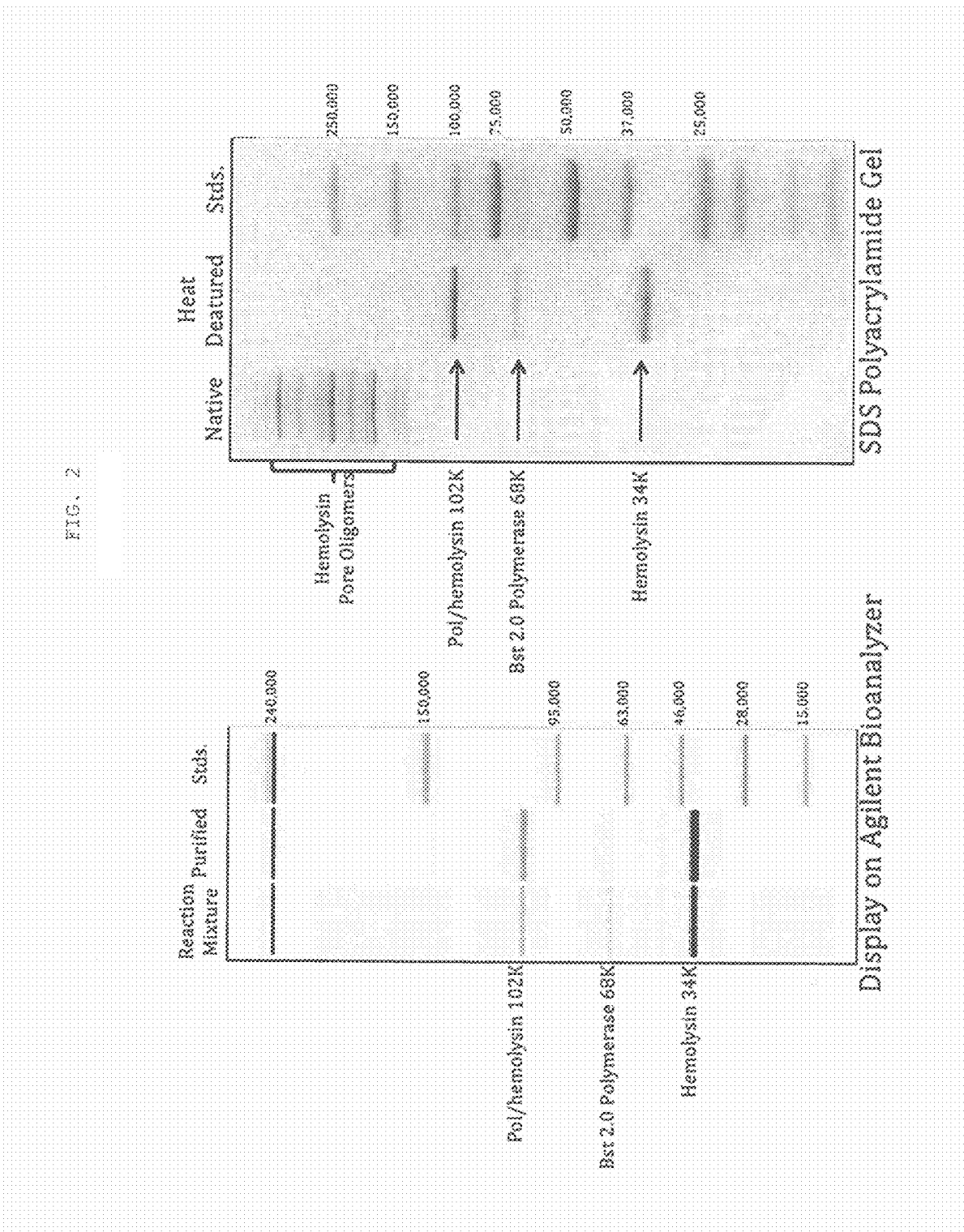
FIG. 2 depicts images of Bioanalyzer and SDS-PAGE gels showing the formation of the conjugate between the pore-forming protein, α-HL-C46, and the DNA polymerase, Bst 2.0, formed in the IEDDA reaction mixtures prepared and carried under conditions as described in Example 1.

The left hand image of FIG. 2, labeled "Display on Agilent Bioanalyzer," shows the comparative Bioanalyzer (Agilent) analysis results of samples taken directly from the reaction mixture and denatured (lane labeled "Reaction Mixture") and reaction mixture further purified on a $Ni^{2+}$ column and then denatured (lane labeled "Purified"). The Reaction Mixture sample shows the three bands expected for the α-HL monomer (labeled "Hemolysin") at a MW of 34,000, the Bsc 2.0 polymerase at a MW of 68,000, and the α-HL-C46 monomer-Bst 2.0 conjugate product at a MW of ~102,000 (labeled "Pol/hemolysin"). The Purified sample results show that the α-HL monomer and α-HL-C46 monomer-Bst 2.0 conjugate product remain but nearly all of the unconjugated Bst 2.0 polymerase was removed. This is as expected because it does not have the necessary His-tag to be retained following the $Ni^{2+}$ column purification.

The right hand image of FIG. 2, labeled "SDS Polyacrylamide Gel" shows the SDS-PAGE of samples taken directly from the reaction mixture and run under non-denaturing conditions (labeled "Native") or following heating at 95° C. for 5 min ("Heat Denatured"). The "Native" lane shows three primary bands in a MW range labeled "Hemolysin Pore Oligomers." The highest MW of the three primary bands is at a MW of ~306,000 as expected for the α-HL heptamer conjugated to a single DNA polymerase. The other two bands are consistent with a 6:1 α-hemolysin pore complex without polymerase attachment. The second lane, labeled "Heat Denatured" shows the reaction mixture after heat denaturation at 98° C. The intense band labeled "Pol/hemolysin" at a MW of ~102,000 is as expected for the predicted product of TCO-modified α-HL-C46 monomer with the 6-Me-TZ-modified DNA polymerase Bst 2.0 (i.e., conjugate reaction product as shown in FIG. 1). The band labeled "Hemolysin" at a MW of ~34,000 is consisted with the expected presence of wild-type α-HL monomer that was part of the heptamer complex but was not labeled with 6-Me-TZ and accordingly did not form a conjugate. The faint band labeled "Bst 2.0 Polymerase" at a MW of ~68,000 is due likely to a small amount of the BST 2.0 polymerase for which the conjugating linker was hydrolyzed.

As described above, these results indicate that the Bst2.0 polymerase conjugate with the 6:1 α-HL pore complex forms nearly quantitatively (>95%) as a result of the IEDDA reaction between 6-Me-TZ-PEG$_4$-Bst 2.0 and TCO-PEG$_3$-α-HL reagents carried out for 1 hour at room temperature. In contrast, the Cu-free azido-DBCO click reaction resulted in less than 5% conversion to conjugate even after 3 days reaction and even though only the α-HL monomer, and not the heptameric complex, was used. Thus, the fast, and nearly quantitative IEDDA reaction provided herein allows for the formation of conjugates between large biomolecules, such as DNA polymerase (~70 kDa) and very large heptameric complexes of pore-forming proteins, such as the 6:1 α-HL pore complex. As described below in Example 2, such conjugates can be inserted in lipid bilayers allowing formation of forming nanopore array detectors.

Example 2

Use of Bst 2.0-α-HL Conjugate in a Nanopore Array

This example illustrates the insertion and use of Bst 2.0-α-BL nanopore conjugates prepared as in Example 1 in membranes formed over an array of 264 individually addressable integrated circuit chips, each comprising a Ag electrode (Genia Technologies, Mountain View, Calif., USA). The array consists of a 264 sensor semiconductor integrated circuit packaged dry in a simple fluidics package along with a reader instrument. Each chip in the array is manufactured in a standard CMOS process with surface modifications to allow for constant contact with biological reagents and conductive salts. Each Ag electrode sensor on the chip is within a single well, allowing formation of a phospholipid bilayer between silver/silver chloride electrodes, and is individually addressable and scalable to denser array counts.

The lipid used in forming the phospholipid bilayer membrane was 1,2-diphytanoyl-sn-glycero-3-phosphocholine (Avanti Polar lipids). This solid was dissolved in decane at 15 mM and then painted in a layer across the 264 wells on the chip-station. A thinning process then was initiated by pumping air through the cis side of the wells, thus reducing multilamellar lipid membranes to a single bilayer. Bilayer formation was tested using a ramping voltage from 0 to 1000 mV. A typical single bilayer would temporarily open between 300 to 500 mV.

After forming the lipid bilayer, a mixture of 0.05 μg of the Bst 2.0-α-HL nanopore conjugate, 3 μM of a 83-mer "SimpleBell" DNA templates, and 30 μM of four 5'-tagged nucleotides was added to the cis side of the chip.

The 83-mer SimpleBell templates are self-priming and have the sequence 5'-GCG CTC GAG ATC TCC TCG TAA GAG GAG ATC TCG AGO GCA CTG ACT GXC TGA CCT CAG CTG CAC GTA AGT GCA GCT GAG GTC AG-3', where X, and first open position on the template, could be any one of the four bases A, C, G or T. The same solution to dissolve DNA (150 mM KCl, 3 mM $SrCl_2$, 20 mM Hepes, pH 7.5 at 25° C.) was used as the electrolyte solution for nanopore ion channel measurements.

5'-tagged nucleotides useful in the nanopore devices as disclosed herein are described in U.S. Provisional Appl. No. 61/369,628, filed Mar. 24, 2014, entitled "Chemical Methods for Producing Tagged Nucleotides" which is hereby incorporated by reference herein for all purposes. Briefly, the 5'-tagged nucleotides are captured by Bst 2.0 DNAP and form a complex in the polymerase active site with the self-priming template. At the same time, the "tail" of the tag moiety becomes positioned in the nanopore under an applied voltage, causing a current decrease compared to the open pore current.

For example, as shown in FIG. 3 using the SimpleBell template shown in FIG. 3a where X=C, the $T_{30}$ oligonucleotide "tail" moiety of the 5'-tagged nucleotide (dG6P-Cy3-

$T_{30}$-$C_6$) is captured by the conjugated Bst 2.0 polymerase enters the α-HL nanopore and produces a consistent current blockade of from about 15 pA open pore current to about 7 pA, with a duration of the current blockade in the millisecond range (FIGS. 3b and 3c).

In other experiments, the four tagged nucleotides used as polymerase substrates in the mixture were: dT6P-Cy3-$T_2$-dSp$_8$-$T_{20}$-$C_3$; dC6P-Cy3-$T_4$-dSp$_3$-$T_{23}$-$C_3$; dG6P-Cy3-$T_{30}$-$C_6$; and dA6P-Cy3-$T_4$-FldT-T-DldT-$T_{23}$-$C_3$. The Bst 2.0-α-HL nanopore conjugate was inserted into the lipid bilayer. A 100 mV (cis vs. trans) voltage was applied across the chip-board between two Ag/AgCl electrodes placed on either side of the membrane and pore. Signals representing four differing current blockade events were observed from the four different 5'-tagged nucleotides as they were captured by the nanopore-polymerase conjugates. Plots were recorded based on the two types of current blockade events observed: (1) blockade amplitudes as percentage of the open pore current, and (2) dwell times in milliseconds. Current blockade events that, lasted longer than 10 ms and that reduced the channel conductance from 0.6 to 0.2 were deemed to be indicative of productive nucleotide capture by the Bst 2.0 polymerase conjugated to the nanopore. These blockade levels and dwell times are tabulated in FIG. 3d.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

REFERENCES

1. Akeson et al., U.S. Pat. No. 6,267,872 (Jul. 31, 2001).
2. Akeson et al., U.S. Pat. No. 6,746,594 (Jun. 8, 2004).
3. Baldarelli et al., U.S. Pat. No. 6,015,714 (Jan. 18, 2000).
4. Blackman et al., "Tetrasine Ligation: Fast Bioconjugation Based on Inverse-Electron Demand Diels-Alder Reactivity," J. Am. Chem. Soc. 130:13518-13519 (2008).
5. Branton et al., U.S. Patent Publication No. 2003/0104428 (Jun. 5, 2003).
6. Branton et al., U.S. Pat. No. 6,627,067 (Sep. 30, 2003).
7. Church et al., U.S. Pat. No. 5,795,782 (Aug. 18, 1996).
8. Davis et al., U.S. Patent Publication No. 2013/0244340 A1 (Sep. 19, 2013).
9. Deader, U.S. Pat. No. 6,617,113 (Sep. 5, 2003).
10. Denison et al., U.S. Pat. No. 6,362,002 (Mar. 26, 2002).
11. Denison et al., U.S. Pat. No. 6,673,615 (Jan. 6, 2004).
12. Fox et al., U.S. Patent Publication No. 2013/0266512 A1 (Oct. 10, 2013).
13. Golovchenko et al., U.S. Pat. No. 6,464,842 (Oct. 15, 2002).
14. Golovchenko et al., U.S. Pat. No. 7,846,738 (Dec. 7, 2010).
15. Jewett and Bertozzi, "Cu-free click cyioaddition reactions in chemical biology," Chem. Soc. Rev., 2010, 39, 1272-1279 (2010).
16. Ju et al., U.S. Patent Publication No. 2013/0264207 A1 (Oct. 10, 2013).
17. Palmer et al., "Staphylococcus aureus alpha-toxin. Production of functionally intact, site-specifically modifiable protein by introduction of cysteine at positions 69, 130, and 186." J. Biol. Chem. 268 (16):11359-11962 (1993).
18. Presolski et al., "Copper-Catalyzed Azide-Alkyne Click Chemistry for Bioconjugation" Current Protocols in Chemical Biology 3: 153-162 (2011).
19. Reiner et al, "The inverse electron demand Diels-Alder click reaction in radiochemistry," J. Label Compd. Radiopharm. 2014, 57:285-290 (2014).
20. Su et al., U.S. Pat. No. 7,005,264 (Feb. 28, 2006).
21. Valeva et al, "Membrane Insertion of the Heptameric Staphylococcal α-Toxin Pore," J. Biol. Chem., 276, 18, pp. 14835-14841 (2001).
22. Wang et al., "Bioconjugation By Copper(I)-Catalyzed Azide-Alkyne [3+2] Cycloaddition," J. Am. Chem. Soc. 125 (11):3192-3193 (2003).
23. Wiessler et al., U.S. Patent Publication No. 2010/0016545 A1 (Jan. 21, 2010).
24. Wiessler et al., U.S. Patent Publication No. 2013/0085271 A1 (Apr. 4, 2013).

What is claimed is:

1. A composition comprising a compound of formula (I),

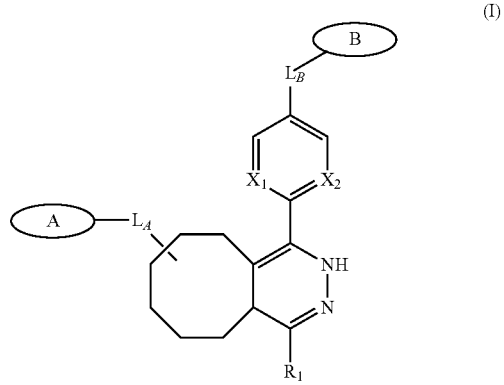

wherein,
one of A and B is a pore-forming protein, and the other is a biomolecule selected from the group consisting of an enzyme, an oligonucleotide of at least 20 nucleotides, an antibody, and a receptor;
$L_A$ and $L_B$ are linkers;
$X_1$ and $X_2$ are atoms independently selected from C and N; and
$R_1$ is a chemical group selected from the group consisting of: H, F, Cl, Br, I, $CH_3$, $CF_3$, $NH_2$, $NO_2$, OH, C(O)OH, C(O)OCH$_3$, C(O)NH$_2$, linear or branched ($C_2$-$C_5$) alkyl, linear or branched ($C_2$-$C_5$) alkenyl, linear or branched ($C_2$-$C_5$) alkynyl, unsubstituted or para-substituted 6-membered aryl ring, and unsubstituted or para-substituted 6-membered heteroaryl ring.

2. The composition of claim 1,
i) wherein the pore-forming protein:
   a) is a part of a multimeric complex, including a heptamer;
   b) is part of a nanopore
   c) is capable of forming a nanopore of a diameter of about 0.5 nanometer to about 25 nanometers;
   d) is embedded in a membrane;
   e) is attached to a solid substrate, including substrates comprising a material selected from the group consisting of polymer, glass, silicon, and a combination thereof; and/or f) is selected from the group consisting of α-hemolysin, α-HL-C46, β-hemolysin, γ-hemolysin, aerolysin, cytolysin, leukocidin, melittin, MspA porin and porin A, and/or ii) wherein the biomolecule:
  a) is an enzyme capable of catalyzing the synthesis of a polymer;
  b) is an enzyme selected from the group consisting of a DNA polymerase, RNA polymerase, reverse transcriptase, terminal transferase, helicase, and DNA ligase;
  c) comprises a large fragment of DNA polymerase from *B. stearothermophilus*;
  d) is DNA polymerase Bst 2.0; and/or
  e) is 9° N polymerase, *E. Coli* DNA Polymerase I, Bacteriophage T4 DNA polymerase, Sequenase, Taq DNA polymerase, 9° N polymerase (exo-)A485L/Y409V or Phi29 DNA polymerase (φ29 DNA Polymerase), and/or iii) wherein the pore-forming protein has a molecular weight of at least 30 kDa and the biomolecule has a molecular weight of at least 50 kDa.

3. The composition of claim 1,
  a) wherein the $X_1$ and $X_2$ atoms are each C, and $R_1$ is a $CH_3$ group,
  b) wherein one or both of the $X_1$ and $X_2$ atoms are N, or
  c) wherein the $R_1$ is an unsubstituted or para-substituted 6-membered aryl ring, or an unsubstituted or para-substituted 6-membered heteroaryl ring selected from the group consisting of: phenyl, benzoic acid, 4-methyl-phenyl, 4-methoxy-phenyl, 4-trifluoromethyl-phenyl, 2-pyridyl, 2-pyridyl-4-methyl, 2-pyridyl-4-carboxylic acid, 2-pyrimidyl, 2-pyrimidyl-4-methyl, and 2-pyrimidyl-4-carboxylic acid.

4. The composition of claim 1, wherein the compound of formula (I) is selected from the group consisting of compounds of formula (Ia) to formula (Iq):

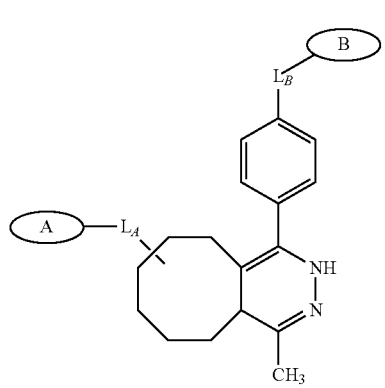
(Ia)

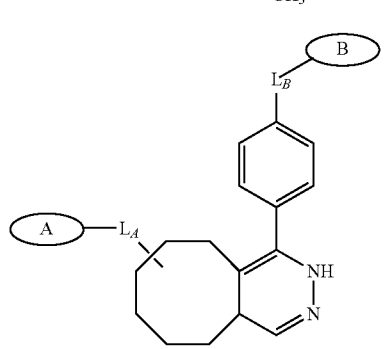
(Ib)

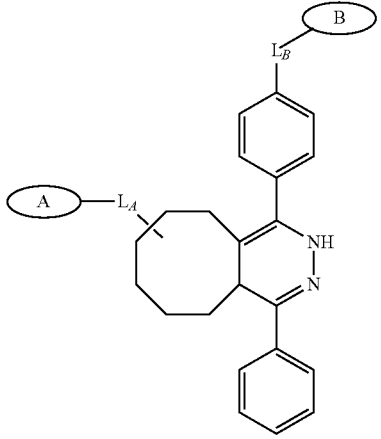
(Ic)

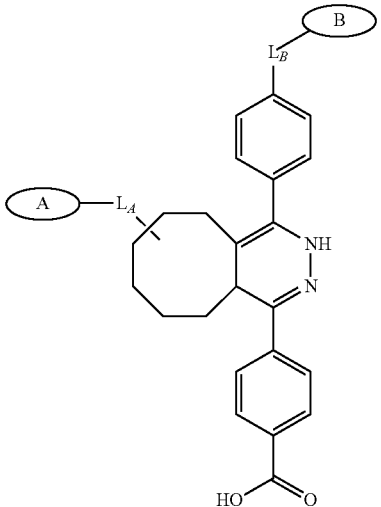
(Id)

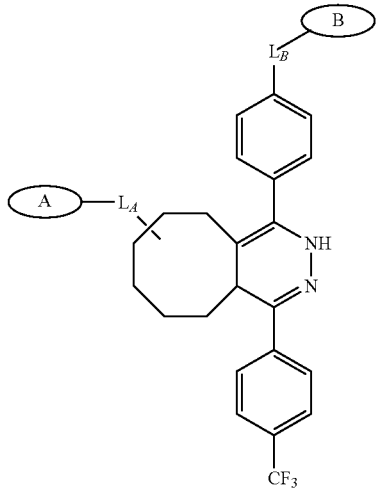
(Ie)

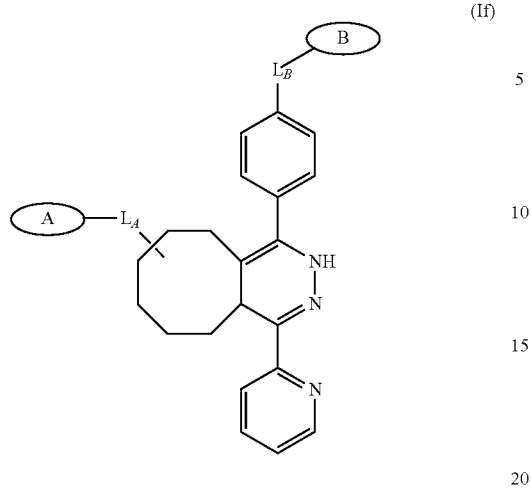
(If)
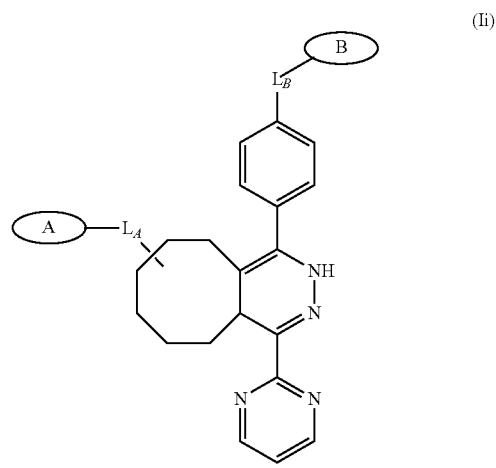
(Ii)
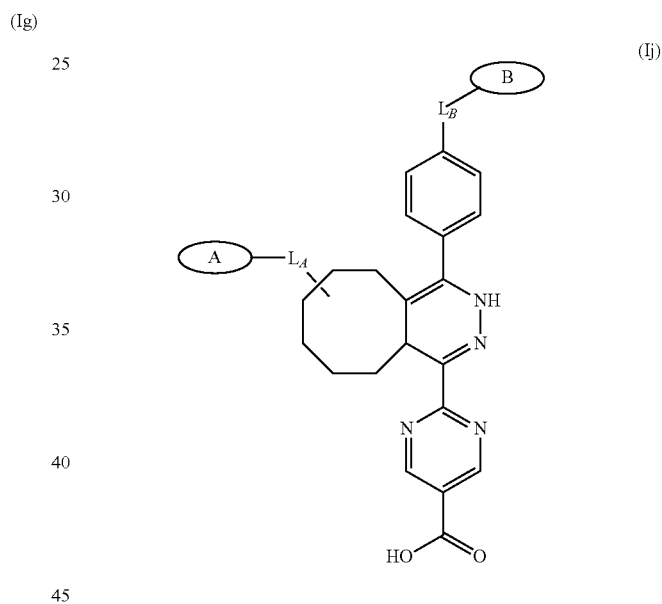
(Ig)
(Ij)
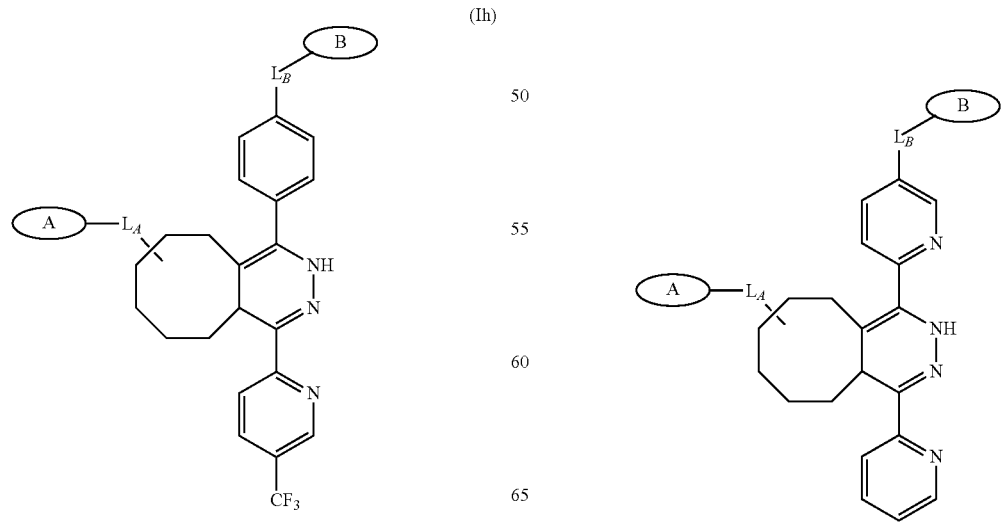
(Ih)
(Ik)

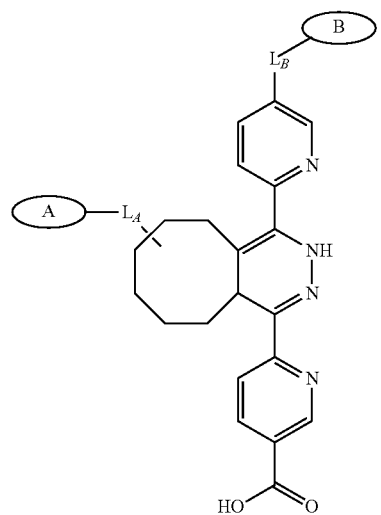 (II)

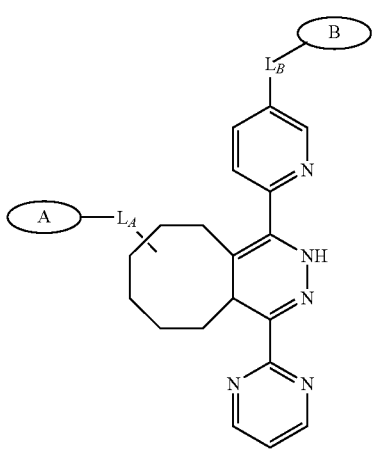 (Im)

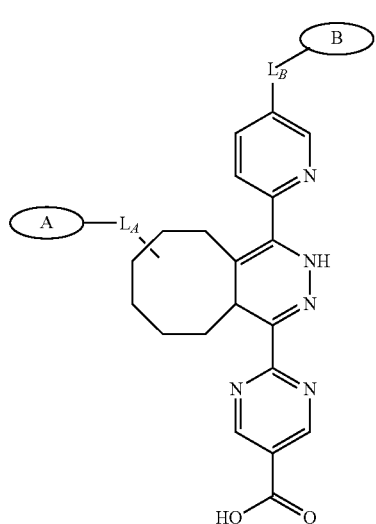 (In)

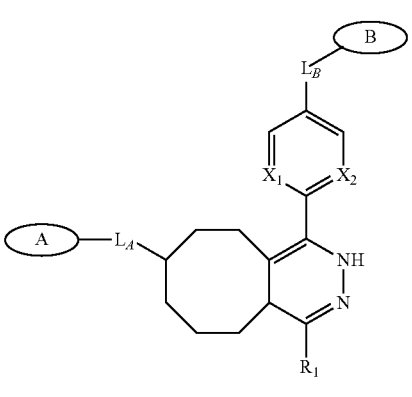 (Io)

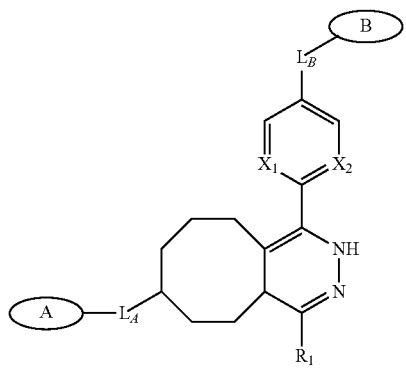 (Ip)

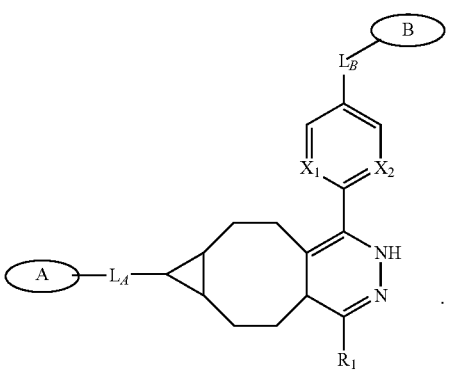 (Iq)

5. The composition of claim 1,
   a) wherein the linkers $L_A$ and $L_B$ comprise a covalently bonded chain of 2 to 100 atoms comprising one or more of the following chemical groups: linear ($C_1$-$C_5$) alkyl, linear ($C_1$-$C_5$) alkenyl, linear ($C_1$-$C_5$) alkynyl, ester, ether, amine, amide, imide, phosphodiester, and/or polyethylene glycol (PEG), and/or
   b) wherein the linkers $L_A$ and $L_B$ attach to A and B either through a thioether bond to a sulfhydryl group on A and/or B, or through a peptide bond to a primary amine group of A and/or B, and optionally wherein the linkers $L_A$ and $L_B$ are attached to A and B, respectively, through a thioether bond to a sulfhydryl group on A and B, and
   c) wherein optionally the linkers $L_A$ and $L_B$ comprise a polymer from 1 to 50 polyethylene glycol (PEG) moieties.

6. The composition of claim 1, wherein the linkers $L_A$ and $L_B$ are independently selected from the group consisting of structures of formula (IVa)-formula (IVd):

(IVa)

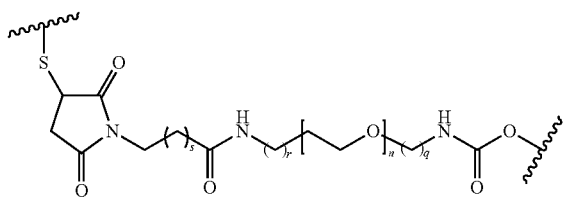

wherein, n=1 to 50, and q, r, and s each independently =0, 1, 2, or 3;

(IVb)

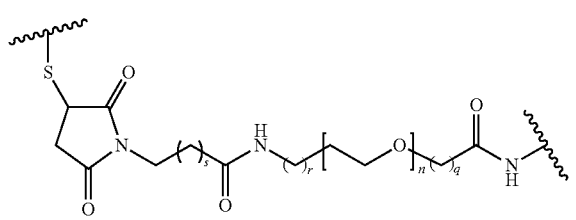

wherein, n=1 to 50, and q, r, and s each independently =0, 1, 2, or 3;

(IVc)

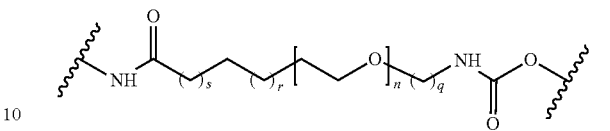

wherein, n=1 to 50, and q, r, and s each independently =0, 1, 2, or 3;

(IVd)

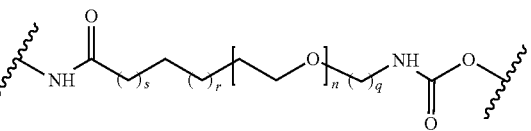

wherein, n=1 to 50, and q, r, and s each independently =0, 1, 2, or 3.

7. The composition of claim 1, wherein the compound of formula (I) are independently selected from the group consisting of structures of formula (Ir), (Is), or (It):

(Ir)

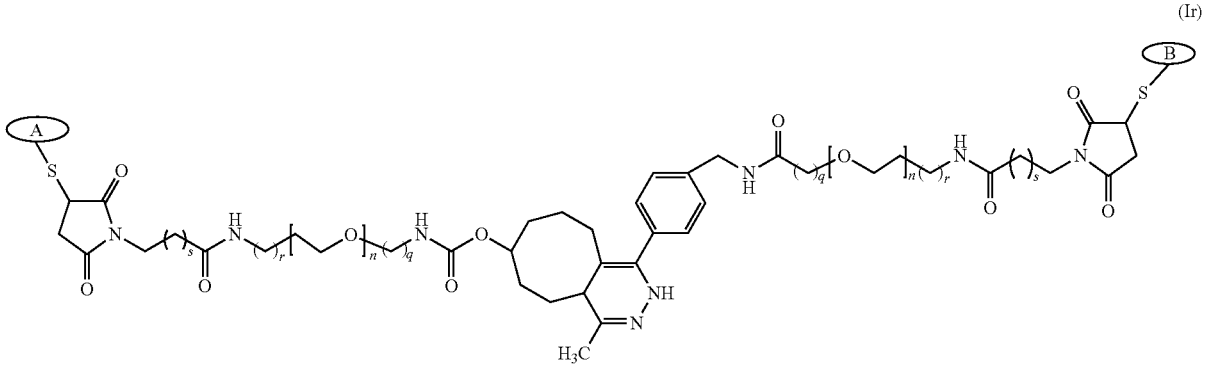

wherein, n=1 to 50, and q, r, and s each independently =0, 1, 2 or 3

(Is)

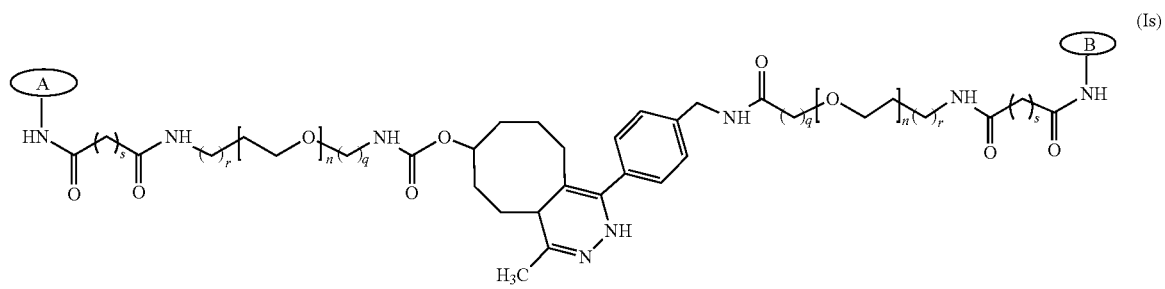

wherein, n=1 to 50, and q, r, and s each independently =0, 1, 2, or 3;

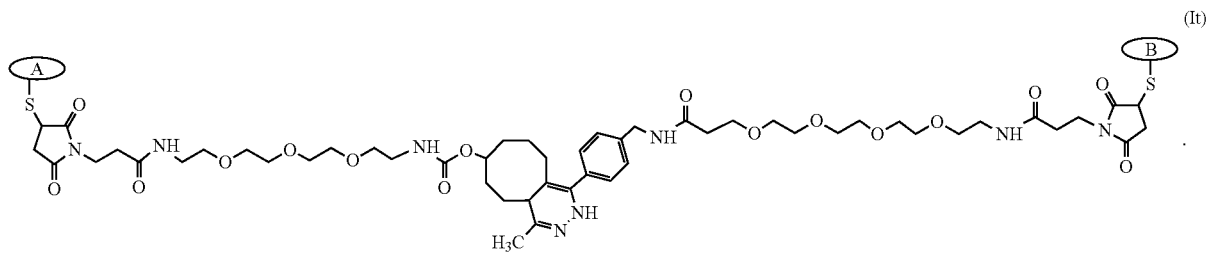

(It)

8. The composition of claim 1, wherein the composition is a nanopore composition.

9. The composition of claim 8, wherein the nanopore comprises a 6:1 ratio of native α-HL monomer to α-HL-C46 monomer, and optionally wherein the nanopore is embedded in a membrane, wherein the membrane is attached to a solid substrate comprising a material selected from the group consisting of: polymer, glass, silicon, and a combination thereof, and wherein the solid substrate comprises a sensor, a sensing circuit, or an electrode coupled to a sensing circuit, optionally, a complementary metal-oxide semiconductor (CMOS), or field effect transistor (FET) circuit.

10. A method of preparing a conjugate of a pore-forming protein and a biomolecule capable of catalyzing the synthesis of a nucleotide polymer, said method comprising contacting under suitable reaction conditions:
a tetrazine-linker-conjugate compound of formula (II)

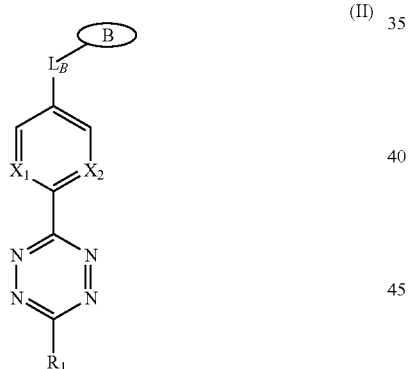

and
a TCO-linker-conjugate compound of formula (III),

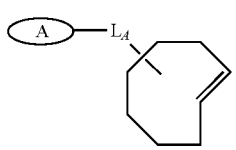

wherein,
one of A and B is a pore-forming protein, and the other a biomolecule capable of catalyzing the synthesis of a nucleotide polymer;

$L_A$ and $L_B$ are linkers;

$X_1$ and $X_2$ are atoms independently selected from C and N; and $R_1$ is a chemical group selected from the group consisting of: H, F, Cl, Br, I, $CH_3$, $CF_3$, $NH_2$, $NO_2$, OH, C(O)OH, $C(O)OCH_3$, $C(O)NH_2$, linear or branched ($C_2$-$C_5$) alkyl, linear or branched ($C_2$-$C_5$) alkenyl, linear or branched ($C_2$-$C_5$) alkynyl, unsubstituted or para-substituted 6-membered aryl ring, and unsubstituted or para-substituted 6-membered heteroaryl ring, including those selected from the group consisting of: phenyl, benzoic acid, 4-methyl-phenyl, 4-methoxy-phenyl, 4-trifluoromethyl-phenyl, 2-pyridyl, 2-pyridyl-4-methyl, 2-pyridyl-4-carboxylic acid, 2-pyrimidyl, 2-pyrimidyl-4-methyl, and 2-pyrimidyl-4-carboxylic acid;

whereby the compounds undergo an inverse electron demand Diels-Alder reaction to form a conjugate of the pore-forming protein and the biomolecule.

11. The method of claim 10, wherein the tetrazine-linker-conjugate compound of formula (II) is a compound of formula (IIo) or (IIp):

(IIo)

![structure]

wherein, n=1 to 50, and q, r, and s each independently=0, 1, 2, or 3;

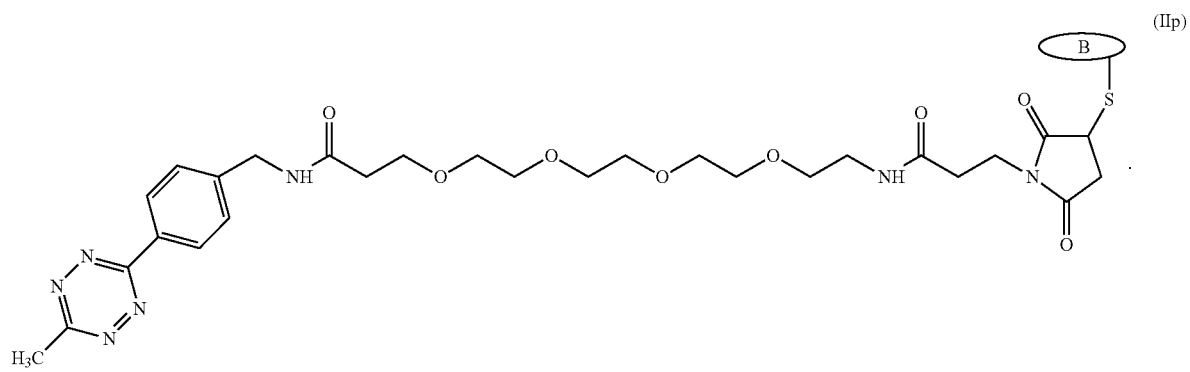
12. The method of claim 10, wherein the TCO-linker-conjugate compound of formula (III) is a compound of formula (IIId) or (IIIe):
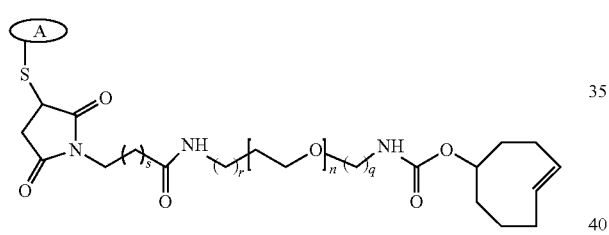
wherein, n=1 to 50, and q, r, and s each independently=0, 1, 2, or 3;
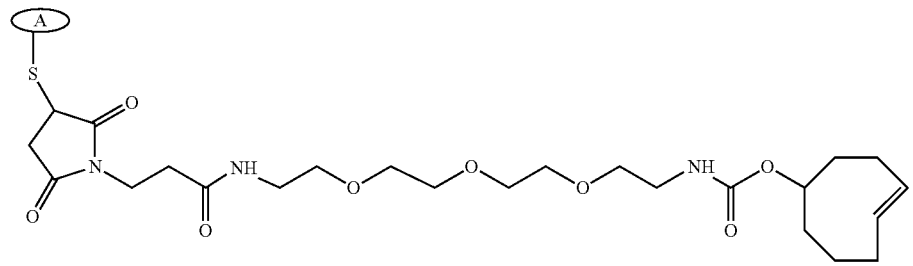

13. A method of preparing a conjugate of a pore-forming protein and a biomolecule capable of catalyzing the synthesis of a nucleotide polymer, said method comprising the steps of:

(a) contacting a pore-forming protein with a tetrazine-linker-maleimide compound of formula (V) under suitable reaction conditions:

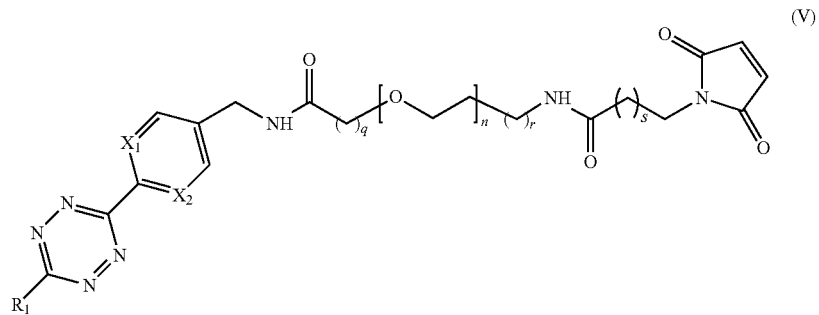

wherein, $X_1$ and $X_2$ are atoms independently selected from C and N;

$R_1$ is a chemical group selected from the group consisting of: H, F, Cl, Br, I, $CH_3$, $CF_3$, $NH_2$, $NO_2$, OH, C(O)OH, C(O)$OCH_3$, C(O)$NH_2$, linear or branched ($C_2$-$C_5$) alkyl, linear or branched ($C_2$-$C_5$) alkenyl, linear or branched ($C_2$-$C_5$) alkynyl, unsubstituted or para-substituted 6-membered aryl ring, and unsubstituted or para-substituted 6-membered heteroaryl ring; and n=1 to 50, and q, r, and s each independently=0, 1, 2, or 3;

thereby forming a tetrazine-linker-pore-forming protein conjugate;

(b) contacting a biomolecule capable of catalyzing the synthesis of a nucleotide polymer with a trans-cyclooctene-linker-maleimide compound of formula (VI) under suitable reaction conditions,

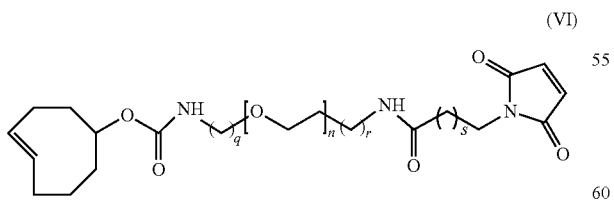

wherein, n=1 to 50, and q, r, and s each independently=0, 1, 2, or 3;

thereby forming a TCO-linker-biomolecule conjugate; and (c) contacting the tetrazine-linker-pore-forming protein conjugate of step (a) with the TCO-linker-biomolecule conjugate of step (b) under suitable reaction conditions, whereby the two conjugates undergo an inverse electron demand Diels-Alder reaction to form a conjugate of the pore-forming protein and the biomolecule.

14. The method of claim 13, wherein the tetrazine-linker-maleimide compound is a compound of formula (Va):

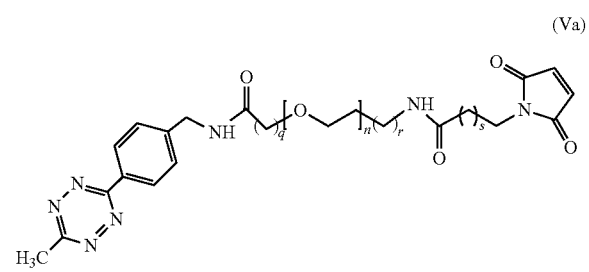

wherein, n=1 to 24, and q, r, and s each independently=1, 2 or 3.

15. The method of claim 13, wherein the tetrazine-linker-maleimide compound is a compound of formula (Va):

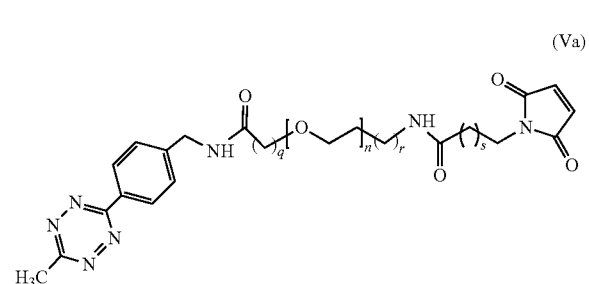

wherein, n=1 to 24, and q, r, and s each independently=1, 2 or 3.

16. The method of claim 13, wherein the TCO-linker-maleimide compound is compound (6):

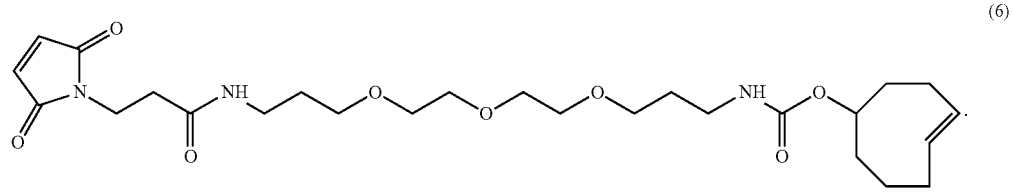 [SMILES: O=C(CCN1C(=O)C=CC1=O)NCCCOCCOCCOCCCNC(=O)OC1CC/C=C/CCC1]

(6)

17. The method of claim 13, wherein the pore-forming protein has a molecular weight of at least 30 kDa and the biomolecule has a molecular weight of at least 50 kDa.

18. The method of claim 13,
i) wherein the pore-forming protein:
   a) is a part of a multimeric complex;
   b) is selected from the group consisting of α-hemolysin, α-HL-C46, β-hemolysin, γ-hemolysin, aerolysin, cytolysin, leukocidin, melittin, MspA porin and porin;
   c) is capable of forming a nanopore of diameter of about 0.5 nanometer to about 25 nanometers;
   d) is embedded in a membrane;
   e) is part of a nanopore;
   f) protein is attached to a solid substrate; and/or
   g) is attached to a solid substrate comprising a material selected from the group consisting of polymer, glass, silicon, and a combination thereof, and/or ii) wherein the biomolecule is
   a) an enzyme capable of catalyzing the synthesis of a polymer;
   b) an enzyme selected from the group consisting of a DNA polymerase, RNA polymerase, reverse transcriptase, terminal transferase, helicase and DNA ligase;
   c) comprises the large fragment of DNA polymerase from *B. stearothermophilus*;
   d) DNA polymerase Bst 2.0; and/or
   e) 9° N polymerase, *E. Coli* DNA Polymerase I, Bacteriophage T4 DNA polymerase, Sequenase, Taq DNA polymerase, 9° N polymerase (exo-)A485L/Y409V or Phi29 DNA polymerase (φ29 DNA Polymerase).

* * * * *